(12) United States Patent

Govindappa et al.

(10) Patent No.: US 12,668,809 B2

(45) Date of Patent: Jun. 30, 2026

(54) MAMMALIAN EXPRESSION VECTORS

(71) Applicant: BIOCON BIOLOGICS INDIA LIMITED, Bangalore (IN)

(72) Inventors: Nagaraja Govindappa, Bangalore (IN); Garima Mishra, Bangalore (IN); P. Vengatapriya, Chennai (IN); Sherene Mathai, Thimvananthapuram (IN); Anuj Goel, Bangalore (IN)

(73) Assignee: Biocon Biologics Limited, Bangalore (IN)

( * ) Notice: Subject to any disclaimer, the term of this patent is extended or adjusted under 35 U.S.C. 154(b) by 1154 days.

(21) Appl. No.: 17/612,345

(22) PCT Filed: May 25, 2020

(86) PCT No.: PCT/IB2020/054930

§ 371 (c)(1),
(2) Date: Jun. 7, 2022

(87) PCT Pub. No.: WO2020/245698

PCT Pub. Date: Dec. 10, 2020

(65) Prior Publication Data

US 2022/0356487 A1      Nov. 10, 2022

(30) Foreign Application Priority Data

Jun. 7, 2019      (IN) .............................. 201941022723

(51) Int. Cl.
*C12N 15/85*      (2006.01)
*C12N 7/00*      (2006.01)
(Continued)

(52) U.S. Cl.
CPC ............... *C12N 15/85* (2013.01); *C12N 7/00* (2013.01); *C12N 9/1025* (2013.01);
(Continued)

(58) Field of Classification Search
CPC ........ C12N 15/85; C12N 7/00; C12N 9/1025; C12N 9/1217; C12N 9/86; C12N 9/93;
(Continued)

(56) References Cited

U.S. PATENT DOCUMENTS 6,596,514 B2      7/2003   Morris et al.
10,113,179 B2   10/2018   Begemann et al.
(Continued)

FOREIGN PATENT DOCUMENTS

CN      106554973 A      4/2017
CN      107881151 A      4/2018
(Continued)

OTHER PUBLICATIONS

WP_000027050, NCBI database, May 2019. (Year: 2019).*
(Continued)

*Primary Examiner* — Robert B Mondesi
*Assistant Examiner* — Naghmeh Nina Moazzami
(74) *Attorney, Agent, or Firm* — Cooley LLP

(57)      ABSTRACT

An expression vector for mammalian cells includes a selection cassette with a nucleotide sequence encoding a glutamine synthetase, operably linked to a PGK promoter and a pA signal. The vector may include the EASE element which is known to promote stable integration of the expression cassettes into the genome. The vector also includes a selection cassette with a nucleotide sequence encoding an enzyme that confers resistance against an antibiotic to a bacterial host as a bacterial selection marker, operably linked to a suitable promoter. The vector further includes an expression cassette for a target polypeptide with an insertion site for a nucleotide sequence encoding the target polypeptide, operably linked to a CMV promoter and a pA signal. The vector also includes a bacterial origin of replication.

10 Claims, 20 Drawing Sheets

Specification includes a Sequence Listing.

(51) Int. Cl.

| | |
|---|---|
| *C12N 9/00* | (2006.01) |
| *C12N 9/10* | (2006.01) |
| *C12N 9/12* | (2006.01) |
| *C12N 9/86* | (2006.01) |
| *C12N 15/113* | (2010.01) |

(52) U.S. Cl.
CPC ............. *C12N 9/1217* (2013.01); *C12N 9/86* (2013.01); *C12N 9/93* (2013.01); *C12N 15/113* (2013.01); *C12Y 207/02003* (2013.01); *C12Y 305/02006* (2013.01); *C12Y 603/01002* (2013.01); *C12N 2710/10343* (2013.01); *C12N 2710/16143* (2013.01); *C12N 2820/55* (2013.01); *C12N 2830/30* (2013.01); *C12N 2830/50* (2013.01)

(58) Field of Classification Search
CPC ........ C12N 15/113; C12N 2710/10343; C12N 2710/16143; C12N 2820/55; C12N 2830/30; C12N 2830/50; C12N 9/10; C12Y 207/02003; C12Y 305/02006; C12Y 603/01002; C12Y 203/01
See application file for complete search history.

(56) References Cited

U.S. PATENT DOCUMENTS

| | | |
|---|---|---|
| 2016/0194660 A1 | 7/2016 | Ye |
| 2017/0101658 A1 | 4/2017 | Goel |

FOREIGN PATENT DOCUMENTS

| | | |
|---|---|---|
| CN | 109837277 A | 6/2019 |
| JP | H11243959 A | 9/1999 |
| JP | 2000503205 A | 3/2000 |
| JP | 2006520589 A | 9/2006 |
| JP | 2018519836 A | 7/2018 |
| WO | WO1997025420 A1 | 7/1997 |
| WO | WO-0077231 A1 | 12/2000 |
| WO | WO-2004081167 A2 | 9/2004 |
| WO | WO-2013137583 A1 | 9/2013 |
| WO | WO-2013161958 A1 | 10/2013 |
| WO | WO-2013186371 A1 | 12/2013 |
| WO | WO2014100073 A2 | 6/2014 |
| WO | WO-2014200557 A1 | 12/2014 |
| WO | WO-2017011598 A1 | 1/2017 |
| WO | WO2019028273 A1 | 2/2019 |
| WO | WO-2020245698 A1 | 12/2020 |

OTHER PUBLICATIONS

Aldrich, et al., Improved bicistronic mammalian expression vectors using expression augmenting sequence element (EASE). Cytotechnology. Nov. 1998; 28(1-3):9-17.
Birch, et al., Antibody production. Advanced drug delivery reviews. Aug. 7, 2006; 58(5-6):671-85.
Extended European Search Report for EP20818406.9, dated May 26, 2023, 6 pages.
GenBank Accession No. AB535097.1, version 1 of the sequence as of Mar. 1, 2014, 3 pages retrieved on Mar. 3, 2025.
GenBank Accession No. AF105229. 1, version 1 of the sequence as of Dec. 22, 1998, 5 pages retrieved on Mar. 3, 2025.
GenBank Accession No. AK390323.1, version 1 of the sequence as of Jan. 11, 2012, 2 pages retrieved on Mar. 3, 2025.
GenBank Accession No. BC051726, version 1 of the sequence as of Oct. 13, 2005, 3 pages retrieved on Mar. 3, 2025.
GenBank Accession No. EU753858.1, version 1 of the sequence as of May 31, 2009, 4 pages retrieved on Mar. 3, 2025.
GenBank Accession No. KF955552. 1, version 1 of the sequence as of Mar. 3, 2014, 3 pages retrieved on Mar. 3, 2025.
GenBank Accession No. KJ796485.1, version 1 of the sequence as of Aug. 16, 2014, 2 pages retrieved on Mar. 3, 2025.
GenBank Accession No. KUL79219.1, version 1 of the sequence as of Jan. 8, 2016, 2 pages retrieved on Mar. 3, 2025.
GenBank Accession No. LT726831.1, version 1 of the sequence as of Feb. 6, 2017, 5 pages retrieved on Mar. 3, 2025.
GenBank Accession No. LT727056.1, version 1 of the sequence as of Feb. 6, 2017, 4 pages retrieved on Mar. 3, 2025.
GenBank Accession No. MG653169. 1, version 1 of the sequence as of May 8, 2018, 2 pages retrieved on Mar. 3, 2025.
GenBank Accession No. MH107058. 1, version 1 of the sequence as of Oct. 30, 2018, 4 pages retrieved on Mar. 3, 2025.
GenBank Accession No. RLQ66161.1, version 1 of the sequence as of Oct. 21, 2018, 2 pages retrieved on Mar. 3, 2025.
GenBank Accession No. X03495.1, version 1 of the sequence as of Oct. 23, 2008, 2 pages retrieved on Mar. 3, 2025.
GenBank Accession No. X16314.1, version 1 of the sequence as of Sep. 24, 2008, 2 pages retrieved on Mar. 3, 2025.
NCBI Accession No. NM_001246770.1, version 1 of the sequence as of Aug. 9, 2022, 2 pages retrieved on Mar. 3, 2025.
SwissProt/UniProt Accession No. A0A3AOYVF2, version 1 of the sequence as of Dec. 5, 2018, 1 page retrieved on Mar. 3, 2025.
SwissProt/UniProt Accession No. G3HG36, version 1 of the sequence as of Nov. 16, 2011, version 30 of the entry of May 23, 2018, 2 pages retrieved on Mar. 3, 2025.
SwissProt/UniProt Accession No. G3IH33, version 1 of the sequence as of Nov. 16, 2011, version 22 of the entry of Dec. 5, 2018, 1 page retrieved on Mar. 3, 2025.
SwissProt/UniProt Accession No. H9AXM0, version 1 of the sequence as of May 16, 2012, version 29 of the entry of Dec. 5, 2018, 2 pages retrieved on Mar. 3, 2025.
SwissProt/UniProt Accession No. O33677, version 1 of the sequence as of Jan. 1, 1998, version 74 of the entry of Dec. 5, 2018, 2 pages retrieved on Mar. 3, 2025.
SwissProt/UniProt Accession No. P04773, version 49 of the sequence as of Jan. 23, 2007, version 107 of the entry of Dec. 5, 2018, 6 pages retrieved on Mar. 3, 2025.
SwissProt/UniProt Accession No. P05364, version 1 of the sequence as of Nov. 1, 1988, version 109 of the entry of Dec. 5, 2018, 3 pages retrieved on Mar. 3, 2025.
SwissProt/UniProt Accession No. P9WKD2, version 1 of the sequence as of Apr. 16, 2014, version 23 of the entry of Dec. 5, 2018, 3 pages retrieved on Mar. 3, 2025.
SwissProt/UniProt Accession No. Q285M4, version 1 of the sequence as of Apr. 4, 2006, version 36 of the entry of May 10, 2017, 2 pages retrieved on Mar. 3, 2025.
SwissProt/UniProt Accession No. Q799Y1, version 1 of the sequence as of Jul. 5, 2004, version 42 of the entry of May 10, 2017, 2 pages retrieved on Mar. 3, 2025.
SwissProt/UniProt Accession No. Q79DR3, version 1 of the sequence as of Jul. 5, 2004, version 116 of the entry of Dec. 5, 2018, 6 pages retrieved on Mar. 3, 2025.
SwissProt/UniProt Accession No. R9URM7, version 1 of the sequence as of Sep. 18, 2013, version 19 of the entry of Dec. 5, 2018, 2 pages retrieved on Mar. 3, 2025.

* cited by examiner

GGGTAGGGGAGGCGCTTTTCCCAAGGCAGTCTGGAGCATGCGCTTTAGCAGCCCCGCTGGGCAC
TTGGCGCTACACAAGTGGCCTCTGGCCTCGCACACATTCCACATCCACGGGTAGGCGCCAACCG
GCTCCGTTCTTTGGTGGCCCCTTCGCGCCACCTTCTACTCCTCCCTAGTCAGGAAGTTCCCCC
CCGCCCCGCAGCTCGCGTCGTGCAGGACGTGACAAATGGAAGTAGCACGTCTCACTAGTCTCGT
GCAGATGGACAGCACCGCTGAGCAATGGAAGCGGGTAGGCCTTTGGGGCAGCGGCCAATAGCAG
CTTTGCTCCTTCGCTTTCTGGGCTCAGAGGCTGGGAAGGGGTGGGTCCGGGGGCGGGCTCAGGG
GCGGGCTCAGGGGCGGGCGGGCGCCCGAAGGTCCTCCGGAGGCCCGGCATTCTGCACGCGTTCA
AAAGCGCACGTCTGCCGCGCTGTTCTCCTCTTCCTCATCTCCGGGCCTTTCTCGATGGCCACCT
CAGCAAGTTCCCACTTGAACAAAAACATCAAGCAAATGTACTTGTGCCTGCCCCAGGGTGAGAA
AGTCCAAGCCATGTATATCTGGGTTGATGGTACTGGAGAAGGACTGCGCTGCAAAACCCGCACC
CTGGACTGTGAGCCCAAGTGTGTAGAAGAGTTACCTGAGTGGAATTTTGATGGCTCTAGTACCT
TTCAGTCTGAGGGCTCCAACAGTGACATGTATCTCAGCCCTGTTGCCATGTTTCGGGACCCCTT
CGGCAGAGATCCTAACAAGCTGGTGTTCTGTGAAGTTTTCAAGTACAACCCGGAAGCCTGCAGAG
ACCAATTTAAGGCACTCGTGTAAACGGATAATGGACATGGTGAGCAACCAGCACCCCTGGTTTG
GAATGGAACAGCAGTATACTCTGATGGGAACAGATGGGCACCCTTTTGGTTGGCCTTCCAATGG
CTTTCCTGGGCCCAAGGTCCGTATTACTGTGGTGTGGGCGCAGACAAAGCCTATGGCAGGGAT
ATCGTGGAGGCTCACTACCGCGCCTGCTTGTATGCTGGGGGTCAAGATTACAGGAACAAATGCTG
AGGTCATGCCTGCCCAGTGGGAATTCCAAATAGGACCCTGTGAAGGAATCCGCATGGGAGATCA
TCTCTGGGTGGCCCGTTTCATCTTGCATCGAGTATGTGAAGACTTTGGGGTAATAGCAACCTTT
GACCCCAAGCCCATTCCTGGGAACTGGAATGGTGCAGGCTGCCATACCAACTTTAGCACCAAGG
CCATGCGGGAGGAGAATGGTCTGAAGCACATCGAGGAGGCCATCGAGAAACTAAGCAAGCGGCA
CCGGTACCACATTCGAGGCTACGATCCCAAGGGGGGCCCTGGACAATGCCCGTCGTCTGACTGGG
TTCCACGAAACGTCCAACATCAACGACTTTTCTGCTGGTGTCGCCAATCGCAGTGCCAGCATCC
GCATTCCCCGGACTGTCGGCCAGGAGAAGAAAGGTTACTTTGAAGACGCCGCGCCTCTGCCAA
TTGTGACCCCTTTGCAGTGACAGAAGCCATCGTCCGCACATGCCTTCTCAATGAGACTGGCGAC
GAGCCCTTCCAATACAAAAACTAA

Fig. 2A: SEQ ID NO: 1

GGGTAGGGGAGGCGCTTTTCCCAAGGCAGTCTGGAGCATGCGCTTTAGCAGCCCCGCTGGGCACTT
GGCGCTACACAAGTGGCCTCTGGCCTCGCACACATTCCACATCCACGGGTAGGCGCCAACCGGCTC
CGTTCTTTGGTGGCCCCTTCGCGCCACCTTCTACTCCTCCCTAGTCAGGAAGTTCCCCCCCGCCC
CGCAGCTCGCGTCGTGCAGGACGTGACAAATGGAAGTAGCACGTCTCACTAGTCTCGTGCAGATGG
ACAGCACCGCTGAGCAATGGAAGCGGGTAGGCCTTTGGGGCAGCGGCCAATAGCAGCTTTGCTCCT
TCGCTTTCTGGGCTCAGAGGCTGGGAAGGGGTGGGTCCGGGGGCGGGCTCAGGGGCGGGCGGGCG
CCCGAAGGTCCTCCGGAGGCCCGGCATTCTGCACGCGTTCAAAAGCGCACGTCTG
CCGCGCTGTTCTCCTCTTCCTCATCTCCGGGCCT

Fig. 2B: SEQ ID NO: 2

```
ATGGCCACCTCAGCAAGTTCCCACTTGAACAAAAACATCAAGCAAATGTACTTGTGCCTGCCCC
AGGGTGAGAAAGTCCAAGCCATGTATATCTGGGTTGATGGTACTGGAGAAGGACTGCGCTGCAA
AACCCGCACCCTGGACTCGTGAGCCCAAGTGTGTAGAAGAGTTACCTGAGTGGAATTTTGATGGC
TCTAGTACCTTTCAGTCTGAGGGCTCCAACAGTGACATGTATCTCAGCCCCTGTTGCCATGTTTC
GGGACCCCTTCCGCAGAGATCCCAACAAGCTGGTGTTCTGTGAAGTTTTCAAGTACAACCGGAA
GCCTGCAGAGACCAATTTAAGGCACTCGTGTAAACGGATAATGGACATGGTGAGCAACCAGCAC
CCCTGGTTTGGAATGGAACAGGAGTATACTCTGATGGGAACAGATGGGCACCCTTTTGGTTGGC
CTTCCAATGGCTTTCCTGGGCCCCAAGGTCCGTATTACTGTGGTGTGGGCGCAGACAAAGCCTA
TGGCAGGGATATCGTGGAGGCTCACTACCGCGCCTGCTTGTATGCTGGGGTCAAGATTACAGGA
ACAAATGCTGAGGTCATGCCTGCCCAGTGGGAATTCCAAATAGGACCCTGTGAAGGAATCGGCA
TGGGAGATCATCTCTGGGTGGCCCGTTTCATCTTGCATCGAGTATGTGAAGACTTTGGGGTAAT
AGCAACCTTTGACCCCAAGCCCATTCCTGGGAACTGGAATGGTGCAGGCTGCCATACCAACTTT
AGCACCAAGGCCATGCGGGAGGAGAATGGTCTGAAGCACATCGAGGAGGCCATCGAGAAACTAA
GCAAGCGGCACGGGTACCACATTGGAGCCTACGATCCCAAGGGGGGCCTGGACAATGCCCGTCG
TCTGACTGGGTTCCACGAAACGTCCAACATCAACGACTTTTCTGCTGGTGTCGCCAATCGCAGT
GCCAGCATCCGCATTCCCCGGACTGTCGGCCAGGAGAAGAAAGGTTACTTTGAAGACCGCCGCC
CCTCTGCCAATTGTGACCCCTTTGCAGTGACAGAAGCCATCGTCCGCACATGCCTTCTCAATGA
GACTGGGGACGAGCCCTTCCAATACAAAAACTAA     Fig. 2C: SEQ ID NO: 3
```

```
GTGATGCCGTTTTGGCAGTACATCAATGGGCGTGGATAGCGGTTTGACTCACGGGGATTTCCAAGT
CTCCACCCCATTGACGTCAATGGGAGTTTGTTTTGGCACCAAAATCAACGGGACTTTCCAAAATGT
CGTAACAACTCCGCCCCATTGACGCAAATGGGCGGTAGGCGTGTACGGTGGGAGGTCTATATAAGC
AGAGCT     Fig. 2D: SEQ ID NO: 4
```

```
GATCTAATTCTGAACTTTTCTTTTGTTCCCTTCCCTTCTACCACACCTAATTGTAATCCATTTTA
ATTCCTGGTCACAGTCCTGTGTCTCCTTCCATTGTACCTTGCCCTTTTCTAAAGAGCGACTGCAA
AGTATGTTTGCGTAGGTGAGGATCTAAAACTTTATGAGGTACGAACATCACAGAATTACTTTGTAA
TTTCAGTTTATTGTAGGCTTGGCTTTTTGGGGAGGGTTACGTCTTAGACCTCTTAGTGCTTCTTTT
GTTTCATGGTGTTCTAACTTCGAAGCATCTCTGTAGCTTTAATGGATTCCTTTTCTGAAAGCTTTG
CTCTCTTTCTTCCCCTCGGCTTTCTCTTAGGCAAGAGGGCTAACTGTAAAGTAAGGCTTACTGCC
TTGTGTTTCCAAATGTGTCCGAAGAGGAAGTGTCTTCTGTGAATCCTGTTATGCATGAATAACAGG
AAATAGAAAGAAATTCACTTTCATTATTATAAAAGTAATATGTTCGTTAAAAAATTCTAATGAAG
AGCTGGAGATGCAACCCAGGGGTAGAGCACACACTCAGCATGCAGGAGGCCCTGGGTCCAATCTTG
GAATCTCCTCTCAGTTAACCTGATCTCTAGCTGATTAGTAGTGAGTGCAAGCCCACTTTCCTCTTC
TGCCTCATTGCTCAGTGATAACAGCTGTTAAACTTTGTCTTATTCTAAAACTACCTCTGTGCAAAT
GCTAGCATAATAATATATATCATATGCACATGATTTTTTTTTTTATCTTGAAAAGTAAGTCAGTATA
GCTACAAAGTTCACTTGGCATTGTCAACATTTCACAGGCCTAATATTCCTCCTCTAGTACTGTCCT
CTTCATTCTTTGTGACCAAGTTTGGAGAGAGTGCACAAATGCCAGGGAGGTTGTGGGAAGGTTTC
```

Fig. 2E: SEQ ID NO: 14 (continued)

```
TCATGTTCTGGTAAGGCGAGTAAGAAAATAGTCTCATGCAGGTGAAATGAGTGCTATGCAGTATAT
ATTATACCAGAGAACAGCAAATGACCAAATTCACACTGAACTAGTTCAGTAAAATTGGCTTTGTCA
AAGCTTTCCTTGCTTAAAATGTAATTCCCTGTCATCCTAGTTCTGGTCTGGATTCTTTTCCTGGAG
TCTTGACTTCCAGATTCCCTGTGGACTTTTGTTTGAGTTTCAAGCTTTTGAAATATAGAAACCTAT
CTAACTTAACAAACTTGGGAGAGAAAGACTCCAGAACAACTGAAAACAGACCAGGCTAAATGAAT
AGACTTTATTCCTCTCTTCTTACCTGCAGTTTTCAGATATGCAGAGTTGGAGCGGATCTTAGAGGT
TGATTCATTCATGCCTGAAGAAAACACATTTTATAGACCCTGTGCCCAAGTTCGTGGTGGACATCA
CCCTTTATTTACTAATTGCACTACATAACAGGCATTTTAGAAGACTGCTCCAGTCAGAGACCCCGC
CTTAGAGGAATCTGTAAACCCTGAACTCCTATCACTCATGAGCACTAGTTATGTTTGGAATGCCGT
ATTAAAACAAAAGTTACATTTCTAAACTTAAAATTTTCTAGCACAGAGACAGTGGGAGTAGCTAAC
TTTGATAGACATTTTTCTACTAAAAGTCTTTCTAAGTACATAATCTTCTGTAAGTTGGAAAACAGC
AAAATAGAACGTCTCCTACGTAGTTAATCTTTTTTGCATAATTTGCACATGTAGGAGTTATTAGTAT
ACGGGTAAGTTTTCACTTTTTCCCCCAACTGGAGTGTCTTGTGGCTGGGTTTGAAAAAGGGAACGG
GAGGCCGCTGGAGGGATTGGTAAATGAGATAAAACACCACTCATTCAACTCAGTGACTCAGCATT
TAAATTTTCCATAAAAGGATTAAAGGAAAATTAAACAAATTCTTAAAGCCAAGACTCTGGAGAAAC
TTGTTGGTGTGCTTTAGTTTTCACTGTTATGACTCATGAATTTATGCATAAATTAGTACATTTATA
AAAACATAGCCTTTTTAGAGTTTTCTGTTTGGCTAAAGTGCCATTGTTAGCATTGGAATTACCTT
TTTATGTCTTATATTTTTTCCAAATAAAAATAAATGTTTCTGCTGTCTTACTACTGAAACTACGTT
GTGAGCACTTTAAATTTCTCAAAGCAGTTTCGCCTGTTATACTTGGCGCTTAGTCATCGTCGTACA
CAACAGGACCTGATTAAGAAGGCTGTGCTGCCTCTAAGCCGGGCTAGATTGTAGCCACTAGCAACC
AGGCTGCAATAATTTCCCTTTGATGACATCATCCACTGTGGAAGAACCCAGTTGCTTCAGCCAGTC
GAACTATACAGTTCCAACCTCATCAAATATGGCATCTCCCTTGCCTGCTATAGCAGGGGGAGGAAA
AAATGCCACCATCTTTTTAATCTAGCAAGCTTCTCTTTTCTTCATCTTTTTTTTTTTTCTTTTAAAA
AAATTCTGATCATGGATGCTTCTTCGGATCCCTATTGCCTTATGACGGGGGAGGAGACAATATCC
CCTTGAGGGAATTACATAAAAGAGGTAAGAGCATCCCCTTGCTCTGAATCCTCTGTTGGTTGTTGT
GCATGCGGCTGGGCGGTTCTGGGACAGGCTGTCTGTTGTCCTCTTGCTGCAATGTGCTGCTTAGT
TGCCCTGCCTTGTTGCTGTGGGAGAATGCGACCTTCCCAGCAGGGCTGGCCCTCCCTGATTGTTTG
CTCTGTGCAGATTAGCCCTGCTTCAGATCACATAGGGCTGCAGACTCCATCTTCTGTGTGAAAATG
CTTTCGGTTTGATTGCAGAAATAAGCTGCCTTTACAGCCAGCTAAAGTCCTGGTGGTTGGTTGGCA
CCTGCAAAGTAGTATTTTTGTACCTCTGGAAACTTATATTTCTTTACACAGCAATATCAAGTGCC
GGTATGCCATTCTGTTTTGGCTGCTGCCAATTACCATGTAGACTTTGCACCACAGAGTAATAGTAA
AAGCTCCTAGCTGCATTTTATAACATTTAAAAATAGCAGGAAAGAAGAATTATTTTTGATTTAACA
TGTTTTTGTCATTTAACGTCTTAACCTGATTGACATACTATATTGTCTGTCTCGTGGGTATCTTGTA
CAACTTGATAGGATAAAGCAATTTAGTTTTTTTTTTTTTTTTTTTAAATACATCCAGAATGTAAGTCG
TCAGTAGTTTCGAACAGATAAGTAATGGTGTTAATCTTTTGGCAGGCTTTGCCTTGGTCTCCTTA
AAGCTAATTAGGTGTTACTTAATTAAACTGCTCTTTTGCTCATTTTCTTAAATTATTTTTTTAAAA
GATAGTTGGCATTTGCTGTTCTAGAAATAAACTTCAAGAAACATTCTTTAGCCAGATGACTTCATG
TATGAGCCATGTTAGTTTGAATTATTTGCTTGGTGTTATAAACTTTATGGTTTAATACCAACTTTT
ATTATGTTTACAAGGTAAATAAGGAAAATTTCAAGTACATTTTGTATCCTGAGAACAAATTTAAGT
TCCATAGAATTTAGGAATTACAATGTATTCAACAGATACTTACTTGTCATACTGTGCCTGCAAAAC
AATAATTAGACTCTGAACAGGTGCAACAATTTTCTGTAGAATTG
```

Fig. 2E: SEQ ID NO: 14

| mAb Codes | mAb description | Fusion details | Fusion location |
|-----------|-----------------|----------------|-----------------|
| Bmab700 | Anti-CTLA4 (Yervoy) | - | (Biosimilar) |
| Fmab 25 | Anti-CD20 fusion | Anti-CD20 mAb + TGFβRII ECD | Fusion at HC C-terminal |
| Fmab 26 | Anti-CD20 fusion | Anti-CD20 mAb+ TGFβRII ECD | Fusion at LC C-terminal |
| Fmab 27 | Anti-CD20 fusion | Anti-CD20 mAb+ TGFβRII ECD | Fusion at HC N-terminal |
| Fmab 28 | Anti-CD20 fusion | Anti-CD20 mAb+ TGFβRII ECD | Fusion at LC N-terminal |

MAMMALIAN EXPRESSION VECTORS

CROSS-REFERENCE TO RELATED APPLICATIONS

This application is filed under provisions of 35 U.S.C § 371 and claims the priority to International Patent Application No. PCT/IB/2020/054930 filed on May 25, 2020 which in turn claims priority to Indian Application No. 201941022723, filed on Jun. 7, 2019, the contents of all is hereby incorporated by reference herein for all purposes.

FIELD OF THE DISCLOSURE

The present disclosure relates to mammalian expression vectors and their use. The invention also provides a method of producing a polypeptide.

SEQUENCE LISTING

This instant application contains a Sequence Listing which has been submitted in text format via EFS-Web and is hereby incorporated by reference in its entirety. Said text copy, created on Nov. 18, 2021, is named 764-003_UTIL_ST25.txt and is 30,919 bytes in size.

BACKGROUND

The following introduction into the background is merely provided to aid the reader in understanding the invention and is not admitted to describe or constitute prior art to the present invention.

Mammalian cells have become the workhorse in bioprocessing of proteins for therapeutic or diagnostic use such as monoclonal antibodies. Today in upstream processing mammalian cell expression systems are the dominant production tool. Desired glycosylation patterns in combination with the development of serum-free and protein-free culture media have paved the way for this expression platform, which is characterized by a suitable cell line and an expression vector. The most commonly used cell line used worldwide is CHO. Production at large scale, combined with an improved understanding of mammalian cell nutritional requirements, have led to substantial optimizations in terms of increased efficiency and yield . . .

Doses of a therapeutic protein in therapeutic use are typically in the range of a few micrograms to milligrams of protein, so that further increase in efficiency and yield are desirable. Furthermore, manufacturing costs in part depend on the expression levels achieved. A critical component of a mammalian expression platform is the expression vector employed.

SUMMARY OF THE DISCLOSURE

The present disclosure can be taken to generally relate to the production of a polypeptide, such as a mammalian polypeptide. Provided is a vector suitable for expressing a respective polypeptide. In a first aspect there is provided an expression vector. The expression vector is a mammalian expression vector. The expression vector includes a selection cassette with a eukaryotic selection marker, a selection cassette with a bacterial selection marker, an expression cassette for a target polypeptide and a bacterial origin of replication. The selection cassette with a eukaryotic selection marker includes a nucleotide sequence that encodes a glutamine synthetase as the eukaryotic selection marker. The nucleotide sequence encoding glutamine synthetase is operably linked to a 3-phosphoglycerate kinase (PGK) promoter and a polyadenylation (pA) signal. The selection cassette with a bacterial selection marker includes a nucleotide sequence that encodes an enzyme which confers resistance against an antibiotic to a bacterial host as the bacterial selection marker, and that is operably linked to a suitable promoter. The expression cassette for a target polypeptide includes an insertion site for a nucleotide sequence that encodes the target polypeptide. The insertion site is operably linked to a cytomegalovirus (CMV) promoter and a polyadenylation (pA) signal.

According to some embodiments the expression vector is a mammalian expression vector. According to some embodiments the expression vector is a vector for a murine or a hamster cell line, such as a CHO cell line or an NS0 (non secreting) myeloma cell line. According to some embodiments the expression vector is an expression vector for CHO cells.

The CMV promoter is generally the human cytomegalovirus immediate early. It is for example found in the pcDNA3.1 or the pCMV vectors.

As noted above, the expression vector includes a selection cassette that includes a nucleotide sequence, which encodes an enzyme conferring resistance against an antibiotic to a bacterial host.

The respective antibiotic is in some embodiments Ampicillin. A suitable enzyme that may be encoded as the bacterial selection marker conferring resistance against Ampicillin to a bacterial host is beta-lactamase.

According to some embodiments of the expression vector the glutamine synthetase encoded by the sequence included in the expression vector has a sequence that is 98% or more identical to SEQ ID NO: 5 and is capable of catalyzing the ATP-dependent conversion of glutamate and ammonia to glutamine.

According to some embodiments the selection cassette with a eukaryotic selection marker includes a nucleotide sequence that encodes a mammalian glutamine synthetase as the eukaryotic selection marker. In some embodiments the glutamine synthetase has a nucleic acid sequence of at least 90% identity to the sequence of SEQ ID NO: 3.

In some embodiments the glutamine synthetase included as a eukaryotic selection marker is a CHO glutamine synthetase. In some embodiments the glutamine synthetase has a nucleic acid sequence of at least 96% identity to the sequence of SEQ ID NO: 3.

In some embodiments the expression vector further includes an expression augmenting sequence element (EASE). In some embodiments the expression vector further includes a selection cassette that includes a nucleotide sequence, which encodes an enzyme that confers resistance against the antibiotic puromycin as a eukaryotic selection marker, operably linked to a 3-phosphoglycerate kinase (PGK) promoter and a polyadenylation (pA) signal. The enzyme that confers resistance against the antibiotic puromycin is in some embodiments puromycin-N-acetyltransferase (pac). According to some embodiments of the expression vector the bacterial origin of replication is the pUC origin of replication.

According to some embodiments the PGK promoter has a sequence of at least 98% identity to SEQ ID NO: 2 and is a functional promoter. According to some embodiments the glutamine synthetase is a CHO glutamine synthetase that has the sequence of SEQ ID NO: 3. According to some embodiments the PGK promoter includes the sequence of SEQ ID NO: 2. According to some embodiments the glutamine synthetase is a CHO glutamine synthetase that includes the sequence of SEQ ID NO: 3. According to some embodiments a sequence that includes the sequence of the respective CHO glutamine synthetase and of the 3-phosphoglycerate kinase (PGK) promoter operably linked thereto has the sequence of SEQ ID NO: 1. According to some embodiments the CMV promoter has the sequence of SEQ ID NO: 4.

According to some embodiments the pA signal is a simian virus 40 pA signal. The simian virus 40 pA signal may in some embodiments be the early pA and late pA signal.

According to some embodiments the bacterial selection marker conferring resistance against Ampicillin to a bacterial host is a beta-lactamase having an identity of 95% to the sequence of SEQ ID NO: 6.

In a second aspect there is provided a recombinant host cell. The host cell includes the expression vector according to the first aspect.

In some embodiments the recombinant host cell is a CHO cell. In some embodiments the recombinant host cell is a NS0 cell. In some embodiments the recombinant host cell is a COS-7 monkey kidney cell. In some embodiments the recombinant host cell is a 3T3 cell. In some embodiments the recombinant host cell is a Baby hamster kidney (BHK) cell. In some embodiments the recombinant host cell is a human embryonic kidney 293 cell.

In a third aspect there is provided a method of producing a polypeptide. The method involves culturing the recombinant host cell according to second aspect under conditions suitable for expressing a heterologous target polypeptide. The recombinant host cell according to second aspect includes an expression vector, in which a nucleotide sequence encoding the polypeptide as a heterologous target polypeptide is included at the insertion site for the nucleotide sequence encoding the target polypeptide.

In typical embodiments of the method according to the third aspect the nucleotide sequence encoding the polypeptide as a heterologous target polypeptide is operably linked to the CMV promoter and to the pA signal.

In some embodiments the method according to the third aspect includes maintaining the host cell, e.g. a CHO cell or a NS0 cell, as a suspension in a suitable medium. In some embodiments the method according to the third aspect includes maintaining the host cell, e.g. a CHO cell or a NS0 cell, at a temperature in the range from 33 to 38° C. The temperature may for instance be chosen as about 37° C.

In a fourth aspect there is provided the use of an expression vector according to the first aspect for expressing a polypeptide at high levels.

In a fifth aspect there is provided the use of a host cell according to second aspect for expressing a polypeptide at high levels.

BRIEF DESCRIPTION OF THE DRAWINGS

FIG. 2A depicts the sequence of SEQ ID NO: 1, which includes the sequence of a CHO glutamine synthetase as a eukaryotic selection marker, operably linked to a PGK promoter. FIG. 2B depicts the sequence of SEQ ID NO: 2, which is a PGK promoter. FIG. 2C depicts the sequence of SEQ ID NO: 3, which is the open reading frame encoding a glutamine synthetase as a eukaryotic selection marker.

FIG. 2D depicts the sequence of SEQ ID NO: 4, the sequence of a CMV promoter. FIG. 2E depicts the sequence of SEQ ID NO: 14, the sequence of an expression augmenting sequence element.

DETAILED DESCRIPTION OF THE INVENTION

Figure 1A:
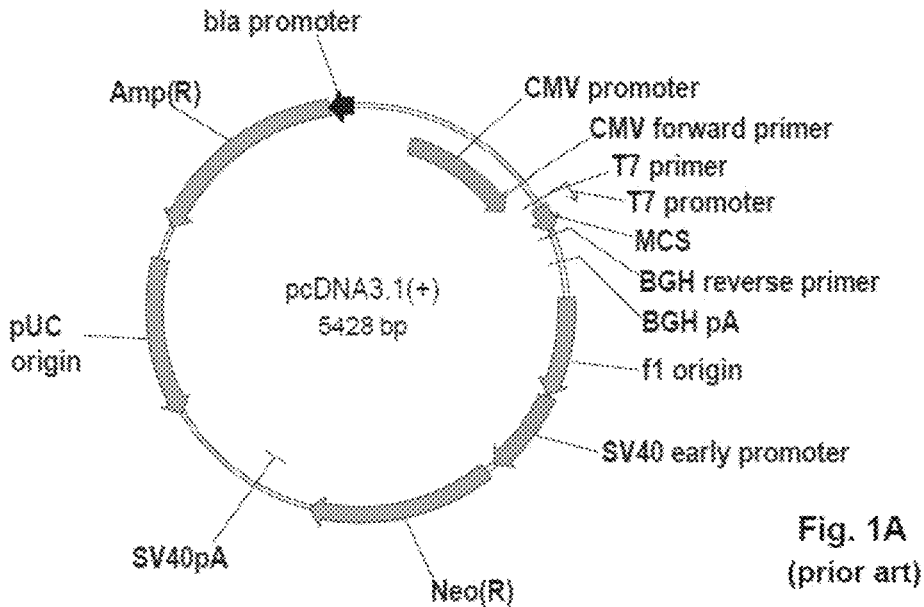
FIG. 1A is a vector map of the known vector pcDNA 3.1 (+), a parent vector for GA fragment 1.

In order that the explanations on the nucleic acid molecules, vectors, host cells, methods and uses disclosed herein may be more readily understood, certain terms are first defined.

Definitions

Unless otherwise stated, the following terms used in this document, including the description and claims, have the definitions given below.

The word "about" as used herein refers to a value being within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. The term "about" is also used to indicate that the amount or value in question may be the value designated or some other value that is approximately the same. The phrase is intended to convey that similar values promote equivalent results or effects according to the invention. In this context "about" may refer to a range above and/or below of up to 10%. The word "about" refers in some embodiments to a range above and below a certain value that is up to 5%, such as up to up to 2%, up to 1%, or up to 0.5% above or below that value. In one embodiment "about" refers to a range up to 0.1% above and below a given value.

The term "essentially consists of" is understood to allow the presence of additional components in a sample or a composition that do not affect the properties of the sample or a composition. As an illustrative example, a pharmaceutical composition may include excipients if it essentially consists of an active ingredient.

The terms "expressing" and "expression" in reference to a polypeptide are intended to be understood in the ordinary meaning as used in the art. A polypeptide is expressed by a cell via transcription of a nucleic acid into mRNA, followed by translation into a polypeptide, which is folded and possibly further processed. With regard to the respective biological process itself, the terms "expression", "gene expression" or "expressing" refer to the entirety of regulatory pathways converting the information encoded in the nucleic acid sequence of a gene first into messenger RNA (mRNA) and then to a protein. Accordingly, the expression of a gene includes its transcription into a primary hnRNA, the processing of this hnRNA into a mature RNA and the translation of the mRNA sequence into the corresponding amino acid sequence of the polypeptide. In this context, it is also noted that the term "gene product" refers not only to a polypeptide, including e.g. a final polypeptide (including a splice variant thereof) encoded by that gene and a respective precursor polypeptide where applicable, but also to the respective mRNA, which may be regarded as the "first gene product" during the course of gene expression.

The terms "expression vector" or "expression construct" refer to a nucleic acid vehicle such as a plasmid, by means of which a desired target polypeptide can be expressed in a host cell using the transcription and translation machinery of the host cell. The nucleic acid molecule can be introduced into the respective host cell and includes one or more regulatory sequences operably linked to nucleic acid sequence that encodes the target polypeptide.

By "fragment" in reference to a polypeptide such as an immunoglobulin or a proteinaceous binding molecule is meant any amino acid sequence present in a corresponding polypeptide, as long as it is shorter than the full length sequence and as long as it is capable of performing the function of interest of the polypeptide—in the case of an immunoglobulin specifically binding to the desired target, e.g. antigen such as PDL-1. The term "immunoglobulin fragment" refers to a portion of an immunoglobulin, often the hypervariable region and portions of the surrounding heavy and light chains that displays specific binding affinity for a particular molecule. A hypervariable region is a portion of an immunoglobulin that physically binds to the polypeptide target.

The term "nucleic acid molecule" as used herein refers to any nucleic acid in any possible configuration, such as single stranded, double stranded or a combination thereof. Examples of nucleic acids include for instance DNA molecules, RNA molecules, analogues of the DNA or RNA generated using nucleotide analogues or using nucleic acid chemistry, locked nucleic acid molecules (LNA), protein nucleic acids molecules (PNA), alkylphosphonate and alkylphosphotriester nucleic acid molecules and tecto-RNA molecules (e.g. Liu, B., et al., J. Am. Chem. Soc. (2004) 126, 4076-4077). LNA has a modified RNA backbone with a methylene bridge between C4' and 02', providing the respective molecule with a higher duplex stability and nuclease resistance. Alkylphosphonate and alkylphosphotriester nucleic acid molecules can be viewed as a DNA or an RNA molecule, in which phosphate groups of the nucleic acid backbone are neutralized by exchanging the P—OH groups of the phosphate groups in the nucleic acid backbone to an alkyl and to an alkoxy group, respectively. DNA or RNA may be of genomic or synthetic origin and may be single or double stranded. Such nucleic acid can be e.g. mRNA, CRNA, synthetic RNA, genomic DNA, cDNA synthetic DNA, a copolymer of DNA and RNA, oligonucleotides, etc. A respective nucleic acid may furthermore contain non-natural nucleotide analogues and/or be linked to an affinity tag or a label.

Many nucleotide analogues are known and can be used in nucleic acids used in the methods of the invention. A nucleotide analogue is a nucleotide containing a modification at for instance the base, sugar, or phosphate moieties. As an illustrative example, a substitution of 2'-OH residues of siRNA with 2'F, 2'O-Me or 2'H residues is known to improve the in vivo stability of the respective RNA. Modifications at the base moiety may be a natural or a synthetic modification of A, C, G, and T/U, a different purine or pyrimidine base, such as uracil-5-yl, hypoxanthin-9-yl, and 2-aminoadenin-9-yl, as well as a non-purine or a non-pyrimidine nucleotide base. Other nucleotide analogues serve as universal bases. Examples of universal bases include 3-nitropyrrole and 5-nitroindole. Universal bases are able to form a base pair with any other base. Base modifications often can be combined with for example a sugar modification, such as for instance 2'-O-methoxyethyl, e.g. to achieve unique properties such as increased duplex stability.

The terms "polypeptide" and "protein" refer to a polymer of amino acid residues and are not limited to a certain minimum length of the product. Where both terms are used concurrently, this twofold naming accounts for the use of both terms side by side in the art.

The terms "polyadenylation site", "poly A site" or "poly A sequence" as used herein refers to a nucleic acid sequence such as a DNA sequence that allows directing both the termination and polyadenylation of a nascent RNA transcript. Efficient polyadenylation of a recombinant transcript is advantageous as a transcript lacking a poly A tail is usually unstable and rapidly degraded. The poly A signal utilized in the vector disclosed herein may be of any origin and may also be "endogenous". An endogenous poly A signal is one that is found naturally at the 3' end of the coding region of a given gene in a genome. A commonly used heterologous poly A signal is the SV40 poly A signal. Examples of suitable polyadenylation sequences also include, but are not limited to the bovine growth hormone (bGH) polyadenylation signal, a beta-globin polyA site, and a herpes simplex virus thymidine kinase polyA site.

The term "purified" is understood to be a relative indication in comparison to the original environment of the cell, thereby representing an indication that the cell is relatively purer than in the natural environment. It therefore includes, but does not only refer to, an absolute value in the sense of absolute purity from other cells (such as a homogeneous cell population). Compared to the natural level, the level after purifying the cell will generally be at least 2-5 fold greater (e.g., in terms of cells/ml). Purification of at least one order of magnitude, such as about two or three orders, including for example about four or five orders of magnitude is expressly contemplated. It may be desired to obtain the cell at least essentially free of contamination, in particular free of other cells, at a functionally significant level, for example about 90%, about 95%, or 99% pure. With regard to a nucleic acid, peptide or a protein, the above applies mutatis mutandis. In this case purifying the nucleic acid, peptide or protein will for instance generally be at least 2-5 fold greater (e.g., in terms of mg/ml).

The word "recombinant" is used in this document to describe a nucleic acid molecule that, by virtue of its origin, manipulation, or both is not associated with all or a portion of the nucleic acid molecule with which it is associated in nature. Generally a recombinant nucleic acid molecule includes a sequence which does not naturally occur in the respective wild type organism or cell. Typically a recombinant nucleic acid molecule is obtained by genetic engineering, usually constructed outside of a cell. Generally a recombinant nucleic acid molecule is substantially identical and/or substantial complementary to at least a portion of the corresponding nucleic acid molecule occurring in nature. A recombinant nucleic acid molecule may be of any origin, such as genomic, cDNA, mammalian, bacterial, viral, semi-synthetic or synthetic origin. The term "recombinant" as used with respect to a protein/polypeptide means a polypeptide produced by expression of a recombinant polynucleotide.

The terms "comprising", "including," "containing", "having" etc. shall be read expansively or open-ended and without limitation. Singular forms such as "a", "an" or "the" include plural references unless the context clearly indicates otherwise. Thus, for example, reference to a "vector" includes a single vector as well as a plurality of vectors, either the same—e.g. the same operon- or different. Likewise reference to "cell" includes a single cell as well as a plurality of cells. Unless otherwise indicated, the term "at least" preceding a series of elements is to be understood to refer to every element in the series. The terms "at least one" and "at least one of" include for example, one, two, three, four, or five or more elements. It is furthermore understood that slight variations above and below a stated range can be used to achieve substantially the same results as a value within the range. Also, unless indicated otherwise, the disclosure of ranges is intended as a continuous range including every value between the minimum and maximum values. The scope and meaning of any use of a term will be apparent from the specific context in which the term is used. Certain further definitions for selected terms used throughout this document are given in the appropriate context of the detailed description, as applicable. Unless otherwise defined, all other scientific and technical terms used in the description, figures and claims have their ordinary meaning as commonly understood by one of ordinary skill in the art.

Provided are vectors, i.e. circular nucleic acid molecules, that are capable of driving high levels of heterologous protein expression in mammalian cells, in particular in CHO cells, as well as methods and uses based thereon. The vectors are replicable in bacterial cells.

Being an expression vector, a vector according to the present disclosure generally includes a promoter, a transcription terminator sequence, an origin of replication, a selectable marker, an insertion site for a nucleotide sequence and a regulatory element.

A promoter is a region of DNA that initiates transcription of a particular gene. A cytomegalovirus promoter is an example of a mammalian expression promoter, being derived from cytomegalovirus. The CMV promoter is commonly used in vectors used in genetic engineering work conducted in mammalian cells, as it is a strong promoter and drives constitutive expression of genes under its control. A promoter is operably linked to the insertion site for a nucleotide sequence encoding the target polypeptide.

A transcription terminator is a portion of nucleic acid sequence that marks the end of a gene or operon in genomic DNA for the transcription process. Such a sequence mediates transcriptional termination by providing a signal in the newly synthesized mRNA that triggers a process which releases the mRNA from the transcriptional complex.

A transcription terminator sequence may be operably linked to the insertion site for a nucleotide sequence encoding the target polypeptide.

An origin of replication, also called replication origin, is a particular sequence in a genome at which replication is initiated. DNA replication typically begins at a single origin of replication.

In *E. coli*, the origin of replication is called oriC. This region is included into an expression vector capable of replicating itself in *E. coli* to form multiple copies.

A selection marker is a gene introduced into a cell, such as a bacterium that confers a trait suitable for artificial selection.

Transcription of eukaryotic genes is regulated by a variety of cis- and trans-acting regulatory elements. Two of the best characterized cis elements are promoters and enhancers. A promoter, see above, is a nucleic acid sequence immediately 5' to the coding sequence of a gene; it includes multiple binding sites for trans-acting transcription factors, forming the basal transcription apparatus. Enhancers generally include multiple binding sites for trans-acting transcription factors but they can be found far upstream or downstream of a coding sequence or even within an intron. A cis element that is included in some embodiments of the vector disclosed herein is the Expression Augmentation Sequence Element (EASE). The EASE element contributes to the stability of the vector which is important for stable cell line development.

An expression vector as disclosed herein includes three distinct expression cassettes. A first cassette is an expression cassette for expressing a selection marker protein that allows the selection of eukaryotic cells that include the vector. This expression cassette is herein also referred to as a selection cassette. A second cassette is an expression cassette for expressing a selection marker protein that allows the selection of bacterial cells that include the expression vector. This expression cassette is herein likewise also referred to as a selection cassette. A third cassette is an expression cassette for expressing a target polypeptide. This expression cassette generally includes a site for inserting a nucleotide sequence that encodes the target polypeptide downstream and in operable linkage to a promoter of the expression cassette.

The insertion site of the third cassette typically contains at least one restriction enzyme recognition sequence. It may include two or more restriction enzyme recognition sequences and define a multiple cloning site. In some embodiments the insertion site includes a recognition sequences for the Not I enzyme. In some embodiments the insertion site includes a recognition sequences for the Xho I enzyme. In some embodiments the insertion site includes a recognition sequences for the BamH I enzyme. In some embodiments the insertion site includes a recognition sequences for the Nhe I enzyme. In some embodiments the insertion site includes a recognition sequences for the EcoR I enzyme. In some embodiments the insertion site includes a recognition sequences for the EcoR V enzyme. In some embodiments the insertion site includes a recognition sequences for the Pme I enzyme. In some embodiments the insertion site includes a recognition sequences for the Afl II enzyme. In some embodiments the insertion site includes a recognition sequences for the Hind III enzyme. In some embodiments the insertion site includes a recognition sequences for the Kpn I enzyme. In some embodiments the insertion site includes a recognition sequences for the Xba I enzyme. In some embodiments the insertion site includes a recognition sequences for the BstX I enzyme. In some embodiments the insertion site includes a recognition sequences for the Pme I enzyme. Cleavage of the circular vector using any one or two of the enzymes for which there is a restriction enzyme recognition sequence creates a linear vector to which a nucleotide sequence encoding the target polypeptide with appropriate ends may be attached.

The three expression cassettes may be arranged in the vector in any order relative to each other.

In some embodiments the first expression cassette for expressing a selection marker protein that allows the selection of eukaryotic cells and the second expression cassette for expressing a selection marker protein that allows the selection of bacterial cells are arranged in the vector in opposite directions. In some embodiments the first expression and the second expression cassette are arranged in the vector in the same direction. In some embodiments the first expression cassette for expressing a selection marker protein that allows the selection of eukaryotic cells and the third expression cassette for expressing a target polypeptide are arranged in the vector in the same direction. In some embodiments the first and the third expression cassette are arranged in the vector in opposite directions. In some embodiments the second expression cassette for expressing a selection marker protein that allows the selection of bacterial cells and the third expression cassette for expressing a target polypeptide are arranged in the vector in opposite directions. In some embodiments the second and the third expression cassette are arranged in the vector in the same direction.

An illustrative example of an order and orientation of the three expression cassettes is shown in FIGS. 1B, 1C, 3 and 4.

A eukaryotic selection marker present in a vector according to the present disclosure is a nucleic acid sequence encoding glutamine synthetase. The enzyme glutamine synthetase is the enzyme responsible for the biosynthesis of glutamine from glutamate and ammonia. This enzymatic reaction provides the only pathway for the synthesis of glutamine in a mammalian cell. In the absence of glutamine in the growth medium, the GS enzyme is essential for the survival of mammalian cells in culture. Mammalian cell lines, such as a Chinese hamster ovary (CHO) cell line, express sufficient GS to survive without exogenous glutamine. GS is the most commonly used selection marker for selecting transfectants while creating stable cell lines. For a cell line in which the endogenous GS in the host is not functional, because of an inactivating mutation or a deletion, supplementation of exogenous GS through the vector allows selection of a transfected population containing the vector of interest. The resultant recombinant cell line can be screened in a glutamine-free medium thereby reducing time, and increasing the probability of obtaining a high titer clone.

On a vector disclosed herein, the enzyme glutamine synthetase is encoded by a nucleic acid sequence that is operably linked to a PGK promoter. PGK is in some embodiments PGK-1. The PGK-1 gene encodes an enzyme of the glycolytic pathway, the housekeeping enzyme, 3-phosphoglycerate kinase. It is therefore ubiquitously expressed. This gene is located on the X chromosome in mammals. In the somatic cells of female mammals only the PGK-1 allele on the active X chromosome is transcribed, the other PGK-1 allele on the inactive X being inert. Hence, PGK-1 is always expressed except for the situation when it is silenced along with most other genes on the inactive X chromosome of female somatic cells or male germ cells. The PGK-1 promoter is thus used for gene expression at high constitutive levels, since it is active in virtually all somatic and germ cell types.

In some embodiments the PGK-1 promoter has the sequence of SEQ ID NO: 2. The PGK-1 promoter of SEQ ID NO: 2 is for example included in a vector depicted in Table 2 of WO 2014/200557. It is also included in the cloning vector PGK1p-Csy4-pA of GenBank accession number KJ796485.1, version 1 dated 16 Aug. 2014 or in the cloning vector PBDGTV of GenBank accession number KU179219.1, version 1 dated 17 Jan. 2017.

In some embodiments the PGK promoter has a sequence that is at least 98% identical to the sequence of SEQ ID NO: 2. As an illustrative example, the mutation introducing vector pMtKCNQ2 DNA of GenBank accession number AB535097.1, version 1 as of 4 Dec. 2009, has a PGK promoter sequence in positions 2984 to 3491 that lacks bases 371 to 382 of SEQ ID NO: 2. As another example, the mPGK1 promoter at positions 6435 to 6924 of the vector pROSA26-DV3 of GenBank accession number LT726831.1, version 1 of 6 Feb. 2017, has six single base deletions relative to the sequence of SEQ ID NO: 2. In some embodiments the PGK promoter has a sequence that is at least 99% identical to the sequence of SEQ ID NO: 2. For example the mouse phosphoglycerate kinase promoter at positions 6566 to 7056 of the plasmid vector pHM2 of GenBank accession number X76683.1, version 1 of 9 Feb. 1994, has five deleted bases and one substitution relative to the sequence of SEQ ID NO: 2. As a further example, the complementary sequence of the PGK-1 promoter at positions 4395 to 4888 of the cloning vector pGZ-DSB-CO of GenBank accession number KY447298.1, version 1 of 22 Feb. 2017, has a deletion of two bases relative to the sequence of SEQ ID NO: 2.

The sequence encoded as CHO glutamine synthetase is in some embodiments the sequence of SEQ ID NO: 5. The sequence is found in GenPept under accession number AJHYQ of 3 Jun. 2002. The sequence encoded as CHO glutamine synthetase is in some embodiments a sequence of 99% or more identity to SEQ ID NO: 5. The sequence may for instance be the sequence encoded by the sequence of SwissProt/UniProt accession number G3HG36, version 1 of the sequence of 16 Nov. 2011, version 30 of the entry of 23 May 2018, which is the sequence encoded by the sequence of GenBank accession number RLQ66161.1, version 1 of 21 Oct. 2018. In some embodiments the sequence encoded as CHO glutamine synthetase is a sequence of 97% or more identity to SEQ ID NO: 5. The sequence encoded as CHO glutamine synthetase is in some embodiments a sequence of 96% or more identity to SEQ ID NO: 5. As an illustrative example, the sequence may be the sequence of SwissProt/ UniProt accession number P04773, version 4 of the sequence of 23 Jan. 2007, version 107 of the entry of 5 Dec. 2018. The sequence encoded as CHO glutamine synthetase includes in some embodiments the sequence of SEQ ID NO: 5. The sequence encoded as CHO glutamine synthetase includes in some embodiments a sequence of 99% identity to SEQ ID NO: 5. The sequence encoded as CHO glutamine synthetase includes in some embodiments a sequence of 99% or more identity to SEQ ID NO: 5. The sequence encoded as CHO glutamine synthetase includes in some embodiments a sequence of 97% or more identity to SEQ ID NO: 5. The sequence encoded as CHO glutamine synthetase includes in some embodiments a sequence of 96% or more identity to SEQ ID NO: 5. In one embodiment the sequence may be the sequence of SwissProt/UniProt accession number G3IH33, version 1 of the sequence of 16 Nov. 2011, version 22 of the entry of 5 Dec. 2018. The sequence encoding CHO glutamine synthetase has in some embodiments the sequence of SEQ ID NO: 3. The sequence encoding CHO glutamine synthetase of SEQ ID NO: 3 is for example included, as positions 147 to 1268, in the sequence of mRNA encoding Chinese hamster glutamine synthetase of GenBank accession number X03495.1, version 1 dated 21 Apr. 1993, the database entry being last updated on 4 Feb. 2011. As a further example, the sequence is found in WO 2013/186371 as SEQ ID NO: 10 or as SEQ ID NO: 1 in EP 2 825 641.

The glutamine synthetase (GS) Gene Expression System (Birch J. R. and Racher A. J., Advanced Drug Delivery Reviews 2006; 58:671-685) is one of two commonly used expression vector systems in monoclonal antibody production. Another common expression system is based on dihydrofolate reductase (DHFR) genes. The GS system is particularly useful for CHO and NS0 cells, being based on the metabolic pathway of glutamate and ammonium to glutamine for the selection of recombinant cells. CHO cells already express endogenous GS. The addition of a selective GS inhibitor, such as methionine sulphoximine (MSX), to a glutamine-free culture medium selects cell clones having integrated the gene construct containing the GS gene.

The sequence encoding glutamine synthetase, e.g. a CHO glutamine synthetase has in some embodiments a sequence that is at least 97% identical to the sequence of SEQ ID NO: 3. The sequence of CHO glutamine synthetase of NCBI accession number NM_001246770.1, version 1 of 9 Oct. 2011, contains at positions 1 to 1116 a promoter sequence that differs in 39 substituted bases from the sequence of SEQ ID NO: 3. In some embodiments the sequence encoding CHO glutamine synthetase has a sequence that is at least 92% identical to the sequence of SEQ ID NO: 3. As an example, the sequence of murine glutamine synthetase of GenBank accession number X16314.1, version 1 of 4 Apr. 1995, has 91 base substitutions relative to the sequence of SEQ ID NO: 3. The sequence encoding CHO glutamine synthetase has in some embodiments a sequence of 90% identity to SEQ ID NO: 3. As an example, the human glutamine synthetase of GenBank accession number BC051726, version 1 of 14 May 2003, has a sequence in positions 1307 to 2422 that differs in 106 substitutions from the sequence of SEQ ID NO: 3. As a further example, the porcine glutamine synthetase of GenBank accession number AK.390323.1, version 1 of 11 Jan. 2012, has a sequence in positions 252 to 1367 that differs in 116 substitutions from the sequence of SEQ ID NO: 3.

The vector of the present disclosure includes a bacterial selection marker. This marker is a nucleotide sequence that encodes an enzyme that provides resistance against an antibiotic to a bacterial host. In some embodiments the enzyme provides resistance to chloramphenicol or to kanamycin and geneticin. In some embodiments the enzyme provides resistance to ampicillin. In some embodiments the enzyme provides resistance to streptomycin and spectinomycin.

An example of an enzyme that provides resistance to a bacterial host against ampicillin is beta-lactamase. In some embodiments the enzyme beta-lactamase has the amino acid sequence of SEQ ID NO: 6, which is the sequence of beta-lactamase of inter alia *Escherichia coli* of SwissProt/ UniProt accession number Q79DR3, version 1 of the sequence of 5 Jul. 2004, version 116 of the entry of 5 Dec. 2018. The sequence is also identical to the synthetic beta-lactamase construct of SwissProt/UniProt accession number Q285M4, version 1 of the sequence of 4 Apr. 2006, version 36 of the entry of 10 May 2017. In some embodiments the beta-lactamase may be a protein with 99% or more identity to the sequence of SEQ ID NO: 6. It may for example be the beta-lactamase protein encoded by the plasmid pPV with the amino acid sequence of the SwissProt/UniProt accession number Q799YI, version 1 of the sequence of 5 Jul. 2004, version 42 of the entry of 10 May 2017. It may also be the class A broad-spectrum beta-lactamase TEM-1 from *Bordetella avium* with the amino acid sequence of the SwissProt/ UniProt accession number A0A3A0YVF2, version 1 of the sequence of 5 Dec. 2018, version 1 of the entry of 5 Dec. 2018.

In some embodiments the beta-lactamase may be a protein with 98% or more identity to the sequence of SEQ ID NO: 6. It may for example be the beta-lactamase protein from *Escherichia coli* with the amino acid sequence of the SwissProt/UniProt accession number R9URM7, version 1 of the sequence of 18 Sep. 2013, version 19 of the entry of 5 Dec. 2018. In some embodiments the beta-lactamase may be a protein with 96% or more identity to the sequence of SEQ ID NO: 6. It may for example be the beta-lactamase protein from *Serratia marcescens* with the amino acid sequence of the SwissProt/UniProt accession number 033677, version 1 of the sequence of 1 Jan. 1998, version 74 of the entry of 5 Dec. 2018. In some embodiments the beta-lactamase may be a protein with 95% or more identity to the sequence of SEQ ID NO: 6.

It may for example be the beta-lactamase protein from *Acinetobacter baumannii* with the amino acid sequence of the SwissProt/UniProt accession number H9AXM0, version 1 of the sequence of 16 May 2012, version 29 of the entry of 5 Dec. 2018.

In some embodiments the beta-lactamase may be a protein with 40% or more identity to the sequence of SEQ ID NO: 6. As an illustrative example, the enzyme beta-lactamase from strain CDC 1551 of *Mycobacterium tuberculosis* having the sequence of the SwissProt/UniProt accession number P9WKD2, version 1 of the sequence of 16 Apr. 2014, version 23 of the entry of 5 Dec. 2018, has a sequence of 381 amino acids, of which 93 are identical to the sequence of SEQ ID NO: 6. In some embodiments the beta-lactamase may be a protein with 2% or more identity to the sequence of SEQ ID NO: 6. As an illustrative example, the enzyme beta-lactamase from *Enterobacter cloacae* with the sequence of the SwissProt/UniProt accession number P05364, version 1 of the sequence of 1 Nov. 1988, version 109 of the entry of 5 Dec. 2018, has a sequence of 381 amino acids, of which 5 are identical to the sequence of SEQ ID NO: 6.

The vector disclosed herein furthermore includes a sequence that encodes an enzyme that confers resistance against the antibiotic puromycin. The respective enzyme may be aminoglycoside phosphotransferase (aph). The enzyme conferring resistance against the antibiotic puromycin may also be blasticidin S deaminase (bsd). The respective enzyme may also be puromycin-N-acetyltransferase (pac).

In some embodiments the sequence encoding the puromycin-N-acetyltransferase may be the sequence of bases 3094 to 3954 of cloning vector pLIF-3 of GenBank accession number KF955552.1, version 1 dated 3 Mar. 2014. This sequence is SEQ ID NO: 7, and is also found e.g. as base positions 6391 to 7251 of the vector of SEQ ID NO: 87 of U.S. Pat. No. 10,113,179 or positions 6565 to 7425 of the vector of SEQ ID NO: 88 or positions 6979 to 7839 of the repair donor cassette of SEQ ID NO: 221 of the same patent. In some embodiments the sequence is the complementary sequence to SEQ ID NO: 7, which is SEQ ID NO: 8. In some embodiments the sequence encoding the puromycin-N-acetyltransferase may be the sequence of the extended spectrum beta lactamase (TEM) gene of *Escherichia coli* strain SRT41, which has GenBank accession number MG653169.1, version 1 dated 8 May 2018. Both sequences encode the amino acid sequence of SEQ ID NO: 6.

The promoter used for the enzyme that provides resistance to a bacterial host against ampicillin may be the beta-lactamase promoter, for example the promoter of the sequence of SEQ ID NO: 9.

The complementary sequence is the sequence of SEQ ID NO: 10.

The vector includes an insertion site for a nucleotide sequence that encodes the target polypeptide to be expressed. The insertion site includes one or more restriction recognition sites for a restriction enzyme. Typically the vector has a multiple cloning site also called a polylinker. A multiple cloning site is a short segment of a nucleic acid sequence which contains a plurality of restriction sites. It may include up to about 20 restriction sites. A restriction site within a multiple cloning site is typically unique, occurring only once within a given plasmid. A multiple cloning site allows the insertion of a gene of interest into the region of the A multiple cloning site. The multiple cloning site generally immediately follows the promoter, and ends before the transcription terminator.

A target polypeptide expressed by a sequence that may be included into the insertion site may be any desired polypeptide. Two illustrative examples are an antibody, including a functional antibody fragment, and an enzyme. Two further illustrative examples are a growth factor and a blood coagulation factor.

The insertion site is operably linked to a CMV promoter. The CMV promoter may be of the sequence of SEQ ID NO: 4. The CMV promoter may also have a sequence that has 99% or more identity to SEQ ID NO: 4. The CMV promoter may for example have or include the sequence of the hCMV immediate early promoter at positions 8186 to 8389 of the cloning vector pHR'-CMVLacZ of GenBank accession number AF105229.1, version 1 of the sequence as of 17 Dec. 1998. As a further example, the CMV promoter may have or include the sequence of the CRU5 chimeric CMV promoter at positions 366 to 569 of the retroviral expression vector L149 of GenBank accession number EU753858.1, version 1 of the sequence as of 31 May 2009. The CMV promoter may in some embodiments have a sequence that has 98% or more identity to SEQ ID NO: 4. It may for example have or include the sequence of the promoter at positions 8806 to 9009 of the Expression vector pDEST152 of GenBank accession number MH107058.1, version 1 of the sequence as of 30 Oct. 2018. As another example, the CMV promoter may have or include the sequence of the hCMV-IE promoter at positions 1053 to 1256 of the mammalian expression vector pACCMVpLpA-E-hRac1-DN of GenBank accession number LT727056.1, version 1 of the sequence as of 6 Feb. 2017.

The vector may include one or more further promoters operably linked to a restriction recognition site for a restriction enzyme, in order to be able to express a desired protein, the sequence for which may be inserted at the respective restriction site. As an example, a promoter of a T7 bacteriophage, such as a promoter of the T7 RNA Polymerase, may be included in the vector. The sequence of SEQ ID NO: 16 is an example of a T7 promoter.

The bacterial replication origin of the vector may be chosen as desired. It is generally a plasmid origin. Typically the origin of replication is a high-copy number origin. In one embodiment the origin is the pMB1 origin. The bacterial origin of replication is in one embodiment the high-copy-number pUC origin. The pUC origin is the most common origin of replication that is used in bacterial vectors. It is derived from the pMB1 origin of the plasmid pBR322 but contains a point substitution within the origin as well as a deletion of the Rop/Rom gene. The letter 'p' indicates that the origin is of a circular, double-stranded DNA molecule, a plasmid. The letters 'UC' stand for "University of California".

In some embodiments the vector further contains an expression augmenting sequence element. Such elements have been disclosed in WO 1997/025420. A DNA sequence formed by ligating two sequences of SEQ ID NO: 1 of WO 1997/025420, namely nucleotides 8672 through 12273 and nucleotides 14290 through 14507 of SEQ ID NO: 1 of WO 1997/025420, has been described as having expression augmenting activity, see Working Example 7 of WO 1997/025420. The sequence of nucleotides 10100 through 14293 of SEQ ID NO: 1 of WO 1997/025420 was likewise disclosed as having expression augmenting activity. Aldrich, T. L., et al, Cytotechnology (1998) 28, 1-3, 9-17, disclose an EASE element termed a "truncated EASE element". A nucleic acid sequence corresponding to a respective DNA sequence may be used as an EASE in the context of the present disclosure.

The expression augmenting sequence element may in some embodiments be a portion of a known EASE. The EASE may in some embodiments include the sequence of SEQ ID NO: 13. The expression augmenting sequence element sequence of SEQ ID NO: 13 is for instance found in US U.S. Pat. No. 6,596,514 in positions 8672 to 12273 of SEQ ID NO: 1 of the document, which has a length of 14507 bases. The EASE sequence of SEQ ID NO: 13 is for instance also included in the CHO sequence of GenBank accession number AF193761.1, version 1 as of 8 Nov. 1998, which has a length of 14462 bases. In this sequence the EASE sequence of SEQ ID NO: 13 defines positions 8627 to 12228 of the sequence of the database entry. In some embodiments the EASE is defined by SEQ ID NO: 13. In some embodiments the EASE is defined by SEQ ID NO: 14. Including the EASE into the vector that contains the PGK promoter, such as a PGK1 promoter-which is operably linked to the nucleotide sequence encoding a glutamine synthetase-leads to increased expression of the nucleotide sequence that encodes the target polypeptide, inserted in frame into the insertion site of the expression cassette. In some embodiments expression is transient expression. Including the EASE into the vector thus in some embodiments leads to high transient expression of the target polypeptide. In this regard the inventors have found that the ability of the EASE to promote stable integration leads to an extended state of the transient gene production period of the vector, relative to the same vector lacking the EASE. As a longer period during which the plasmid is retained in the host cell, causing expression of the target polypeptide, leads to more target polypeptide being produced, the overall amount of target polypeptide produced is increased.

A target polypeptide that may be expressed by an expression vector according to the present disclosure may for example be a therapeutic polypeptide. Two illustrative examples of a therapeutic polypeptide are an adhesion molecule and a cytokine. Two further illustrative examples of a therapeutic polypeptide are an enzyme and a receptor. Another example of a therapeutic polypeptide is a lymphokine. Antibody light and/or heavy chains are yet further example of a therapeutic polypeptide. In some embodiments, the expression vector is adapted to express two target polypeptides, such as the individual polypeptide chains of a heterodimeric protein.

In some embodiments a vector as disclosed herein may contain two target polypeptide expression cassettes. These two target polypeptide expression cassettes may in some embodiments be identical in composition. Once sequences encoding the respective target polypeptide have been inserted into the vector, the target polypeptide expression cassettes in this case only differ in the sequences encoding the target polypeptides. In some embodiments two such target polypeptide expression cassettes are arranged in tandem in the vector.

A method as well as a use that employ an expression vector as disclosed herein may be a method or use, respectively, in which a polypeptide is being produced. Such a polypeptide is herein also termed the "target polypeptide". The method or use may be a method or use for achieving an improved yield of target protein. Such a method or use may involve culturing a recombinant host cell, such as a CHO or NS0 host cell which includes an expression vector as disclosed herein. In such an embodiment the expression vector generally includes a sequence that encodes the target polypeptide. As explained above, such a sequence is included at an insertion site for a nucleotide sequence encoding the target polypeptide. The respective sequence is typically in frame with the cytomegalovirus (CMV) promoter. In some embodiments the nucleotide sequence encoding the target polypeptide is in frame with the PGK promoter and the nucleotide sequence encoding a glutamine synthetase that are included in the selection cassette.

A respective method or use may involve culturing the host cell in a batch or in a fed-batch process. A respective method or use may also involve culturing the host cell in continuous mode. The cells are generally cultured under conditions allowing or promoting expression of the polypeptide. A respective method or use may include recovering the polypeptide.

A respective method or use may also include selecting the host cell on the basis of the presence of the selection cassette that contains the sequence encoding a glutamine synthetase, thereby leading to glutamine synthetase expression. The host cell may in this regard be cultured in the absence of glutamine in the culture medium.

Any number of steps of a method according to the present disclosure, including the entire method, may be performed in an automated way—also repeatedly, using for instance commercially available robots. Computer executable instructions may for instance control data analysis or control mechanical courses of movements employed in a respective method.

The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention.

This includes the generic description of the invention with a proviso or negative limitation removing any subject matter from the genus, regardless of whether or not the excised material is specifically recited herein.

Other embodiments are within the appending claims. In addition, where features or aspects of the invention are described in terms of Markush groups, those skilled in the art will recognize that the invention is also thereby described in terms of any individual member or subgroup of members of the Markush group.

In order that the invention may be readily understood and put into practical effect, particular embodiments will now be described by way of the following non-limiting examples.

Examples

The examples illustrate the generation and use of expression vectors based on the vector pcDNA 3.1 (+).

Material

List of Enzymes:

| No. | Restriction Enzymes | Manufacturer | Catalog Number |
| --- | --- | --- | --- |
| 1 | NdeI | NEB | R0111S |
| 2 | NotI | NEB | R0189S |
| 3 | PvuI | NEB | R0150S |

18

-continued

| No. | Restriction Enzymes | Manufacturer | Catalog Number |
| --- | --- | --- | --- |
| 4 | NruI | NEB | R0192S |
| 5 | EcoRV | NEB | R0195S |
| 6 | BglII | NEB | R0144S |
| 7 | BamHI | NEB | R0136S |
| 8 | SalI | NEB | R0138S |
| 9 | SphI | NEB | R0182S |
| 10 | SmaI | NEB | R0141S |
| 11 | SacI | NEB | R0156S |

List of Kits:

| No. | Name of the Kit | Manufacturer | Catalog number |
| --- | --- | --- | --- |
| 1 | Qiagen quick gel extraction kit | Qiagen | K210012 |
| 2 | Qiaprep Spin Mini prep kit | Qiagen | 27106 |
| 3 | Endofree-Maxi prep kit | Qiagen | 12362 |

Reagents:

| No. | Reagent | Manufacturer | Catalog number |
| --- | --- | --- | --- |
| 1 | Ethidium Bromide | SIGMA | E8751-1G |
| 2 | 1 kb Marker | Thermo Scientific | SM0311 |

Media Components Used:

| No. | Media Name | Manufacturer | Catalog Number |
| --- | --- | --- | --- |
| 1 | LB Agar | Himedia | M557 |
| 2 | LB Broth | Himedia | M575 |

Strains Used:

| No. | Strains and vectors | Company | Catalog Number |
| --- | --- | --- | --- |
| 1 | *E coli* Top-10 | Invitrogen | NAP |

Procedure

In order to assemble four vectors, three fragments were designed and synthesized from geneart named—GA Fragment 1: pMBL C-GS, GA Fragment 2: Puromycin gene fragment, and GA Fragment 3: EASE Reference/Source for these three fragments is given below:

Source for GA fragment 1: pMBL C-GS

TABLE 1

| No. | vector component in pcDNA 3.1 (+) | Location (bp) | Modification for pMBL C-GS |
| --- | --- | --- | --- |
| 1 | NAP | 12 | AG changed to AGATCTG to introduce BglIIsite |
| 2 | CMV promoter | 232-819 | No modification |
| 3 | Multiple cloning site | 863-882 | Modification to include - NotI, XhoI, and BamHI site |
| 4 | BGH polyadenylation sequence | 1028-1252 | It was removed and replaced with sv40 pA from pCHO1.0 |
| 5 | f1 origin | 1298-1726 | The sequence from 1298-3234 was deleted and replaced with PGK- |
| 6 | sv40 early promoter and origin | 1731-2074 | |

TABLE 1-continued

| No. | vector component in pcDNA 3.1 (+) | Location (bp) | Modification for pMBL C-GS |
|---|---|---|---|
| 7 | Neomycin resistance gene (ORF) | 2136-2930 | GS selection cassette |
| 8 | sv40 early polyadenylation signal | 3104-3234 | No modification |
| 9 | pUC origin | 3617-4287 | No modification |
| 10 | Ampicillin resistance gene | 4432-5428 | No modification |
| 11 | SalI restriction site | 5427 | C changed to A, to remove SalI site |

Figure 1B:
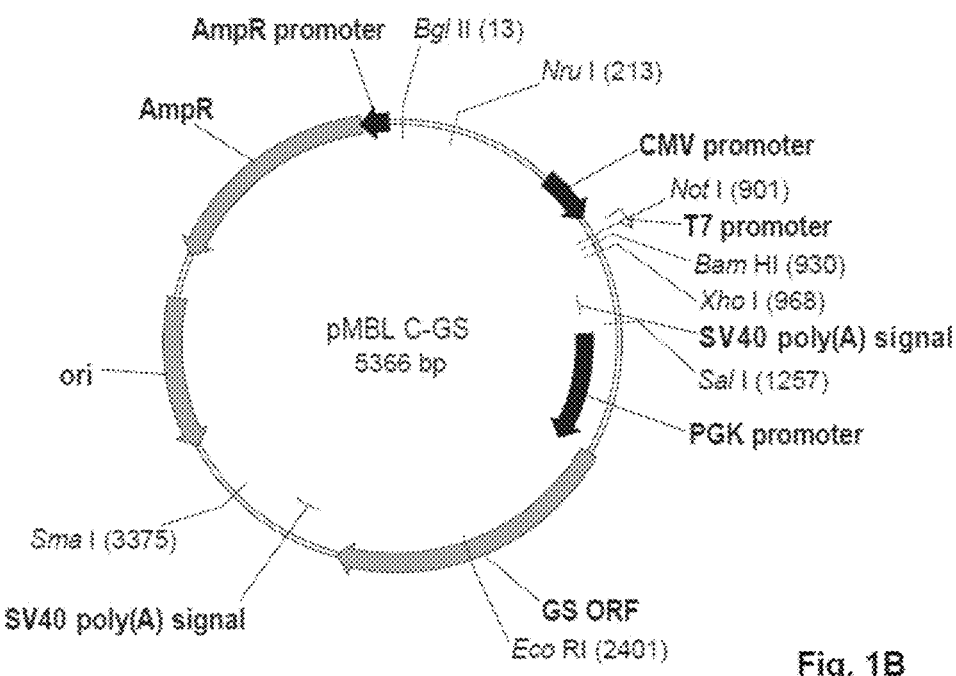
FIG. 1B is a vector map of pMBL C-GS.
Figure 1C:
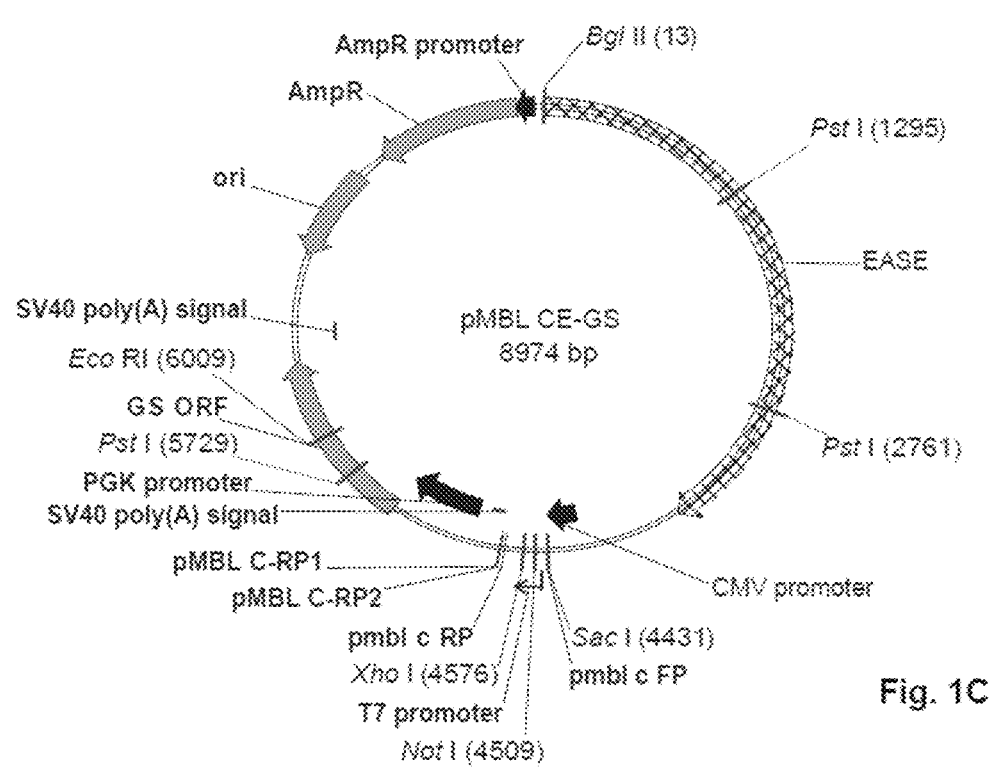
FIG. 1C is a vector map of pMBL CE-GS.
Figure 1D:
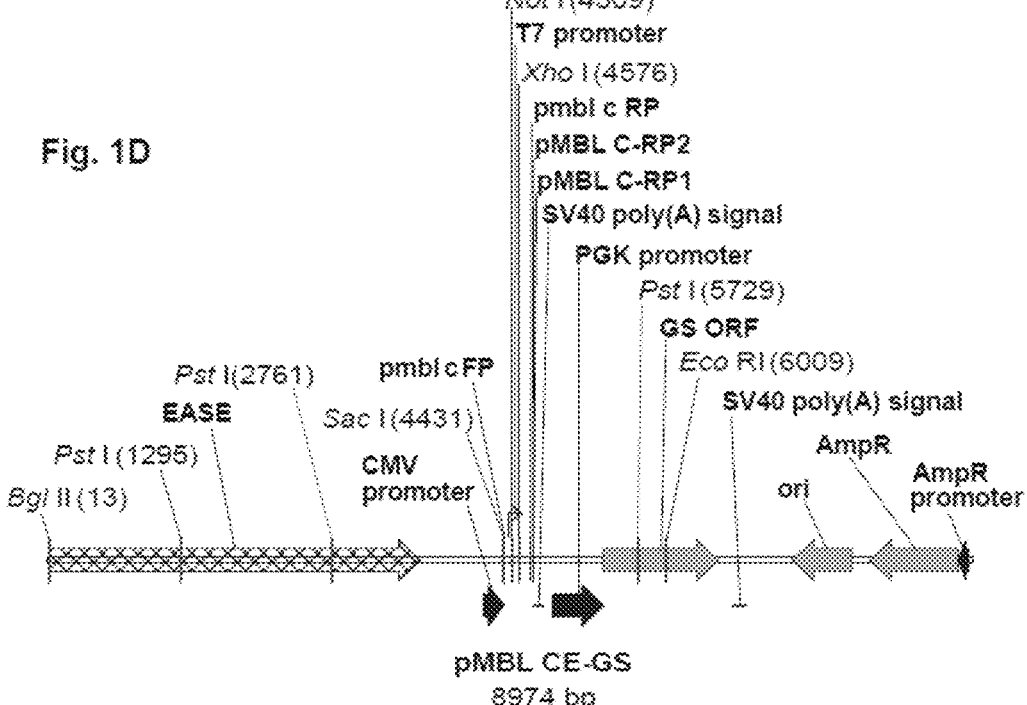
FIG. 1D is a linear display of the vector pMBL CE-GS.
Figure 3:
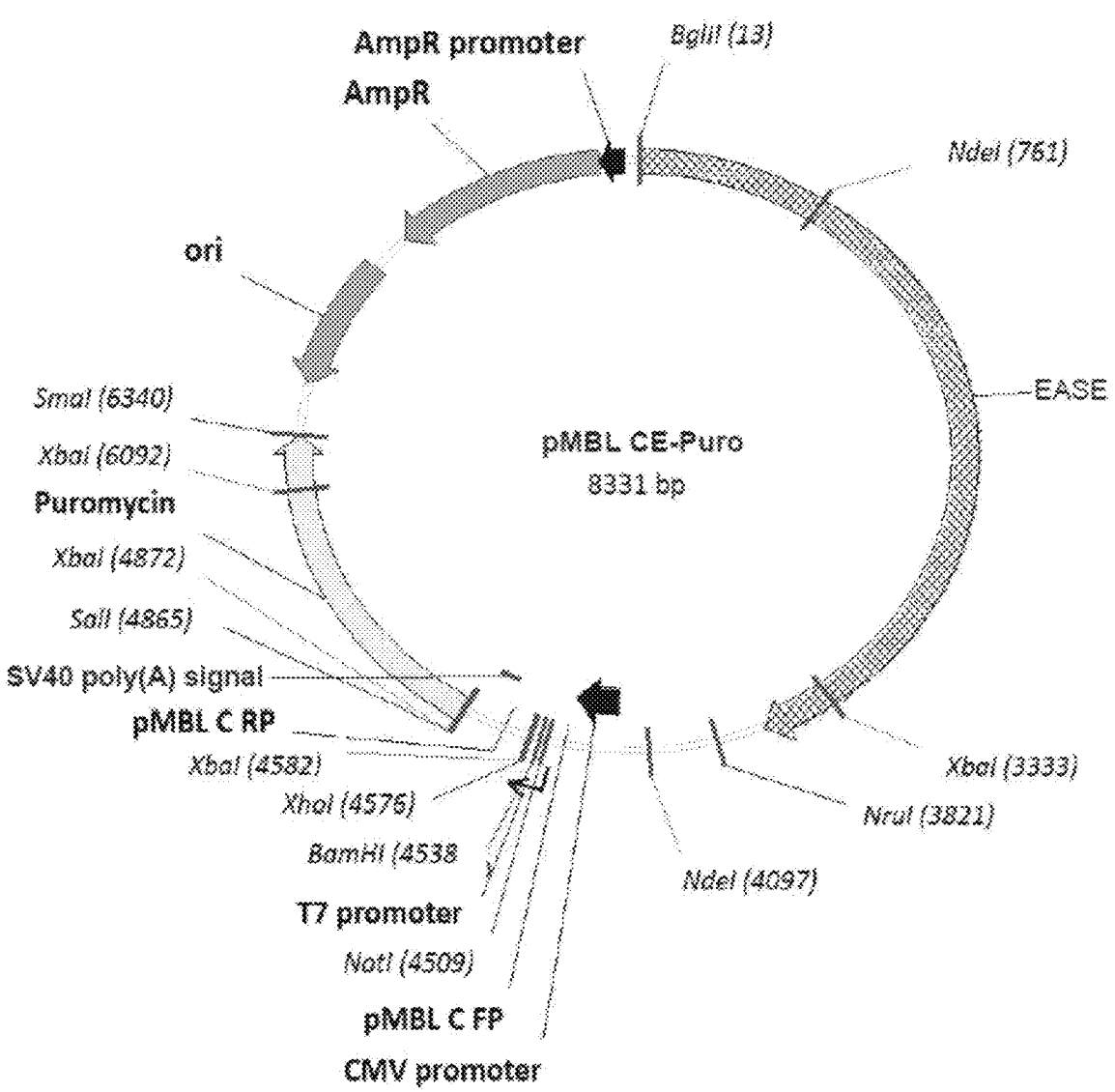
FIG. 3 is a vector map of pMBL CE-Puro.

A vector map of pcDNA 3.1 (+), which is a parent vector for the GA fragment 1, is shown in FIG. 1A. The modifications were made using Vector NTI Version 11.5.1 to parent in-house vector. The in-house vector map of resultant vector pMBL C-GS is shown in FIG. 1B. The specific modifications are captured in the table above.

Reference for Puromycin (GA Fragment 2):

The puromycin gene cassette was sourced from the pCHO1.0 vector from Invitrogen. The gene for puromycin was synthesized from GA with a SalI site at the 5' and SmaI site at the 3' end of the sequence.

Reference for EASE (GA Fragment 3):

The EASE fragment was sourced from GenBank accession number AF193761.1-8672 bp to 12274 bp. The sequence was ordered from Geneart with a BglII site at the 5' end and a BamHI site at the 3' end of sequence.

Process Workflow

The three fragments were synthesized from geneart and reference for each is given in Table 1 above:

1. GA Fragment 1: pMBL C-GS
2. GA Fragment 2: Puromycin gene fragment (labelled as 16AA4TQC_PURO_pMK-RQ)
3. GA Fragment 3: EASE (labelled as 16AASA2C_Frag_3_pMK from GA)

Reconstitution of lyophilized GA fragments, propagation, plasmid isolation, and glycerol stock preparation

The following four in-house vectors were assembled:

1. pMBL CE-GS
2. pMBL CE-Puro 3. pMBL C-Puro 4. pMBL C-GS (Received from geneart)

Creation of pMBL CE-GS:

Cloning of EASE (GA Fragment 3) at BglII site in pMBL C-GS

Creation of pMBL CE-Puro:

Cloning of puromycin gene (GA Fragment 2) at SalI-SmaI site in pMBL CE-GS

Creation of pMBL C-Puro:

Cloning of puromycin gene (GA Fragment 2) at SalI-SmaI site in pMBL C-GS

The following Table 2 provides a summary on the assembled vectors.

TABLE 2

| Nomenclature | EASE | hCMV promoter | MCS | SV40 pA | PGK-GS | SV40 pA | PUC origin | Ampicillin marker | Puromycin resistant gene | Total size (in bp) |
|---|---|---|---|---|---|---|---|---|---|---|
| pMBL CE-GS | Y | Y | Y | Y | Y | Y | Y | Y | N | 8974 |
| pMBL CE-Puro | Y | Y | Y | Y | N | N | Y | Y | Y | 8331 |
| pMBL C-Puro | N | Y | Y | Y | N | N | Y | Y | Y | 4723 |
| pMBL C-GS | N | Y | Y | Y | Y | Y | Y | Y | N | 5366 |

| No. | Nomenclature | pMBL CE-GS | pMBL CE-Puro | pMBL C-Puro | pMBL C-GS |
|---|---|---|---|---|---|
| 1 | EASE | Yes | Yes | No | No |
| 2 | hCMV promoter | Yes | Yes | Yes | Yes |
| 3 | MCS | Yes | Yes | Yes | Yes |
| 4 | SV40 pA | Yes | Yes | Yes | Yes |
| 5 | PGK-GS | Yes | No | No | Yes |
| 6 | SV40 pA | Yes | No | No | Yes |
| 7 | PUC origin | Yes | Yes | Yes | Yes |
| 8 | Ampicillin marker | Yes | Yes | Yes | Yes |
| 9 | Puromycin resistance gene | No | Yes | Yes | No |
| | Total size (in bp) | 8974 | 8331 | 4723 | 5366 |

Characterization of Vector pMBL C-GS

The vector pMBL C-GS was obtained from Geneart (GA Fragment 1) was re-suspended in 25 μL of sterile water to obtain a final concentration of 200 ng/μL.

1 μL was transformed to CCB00024/CHE chemically competent cells. A single colony was streaked and inoculated for plasmid isolation. The overnight culture was then stored as a glycerol stock. The plasmid was isolated.

Figures 4, 5A:
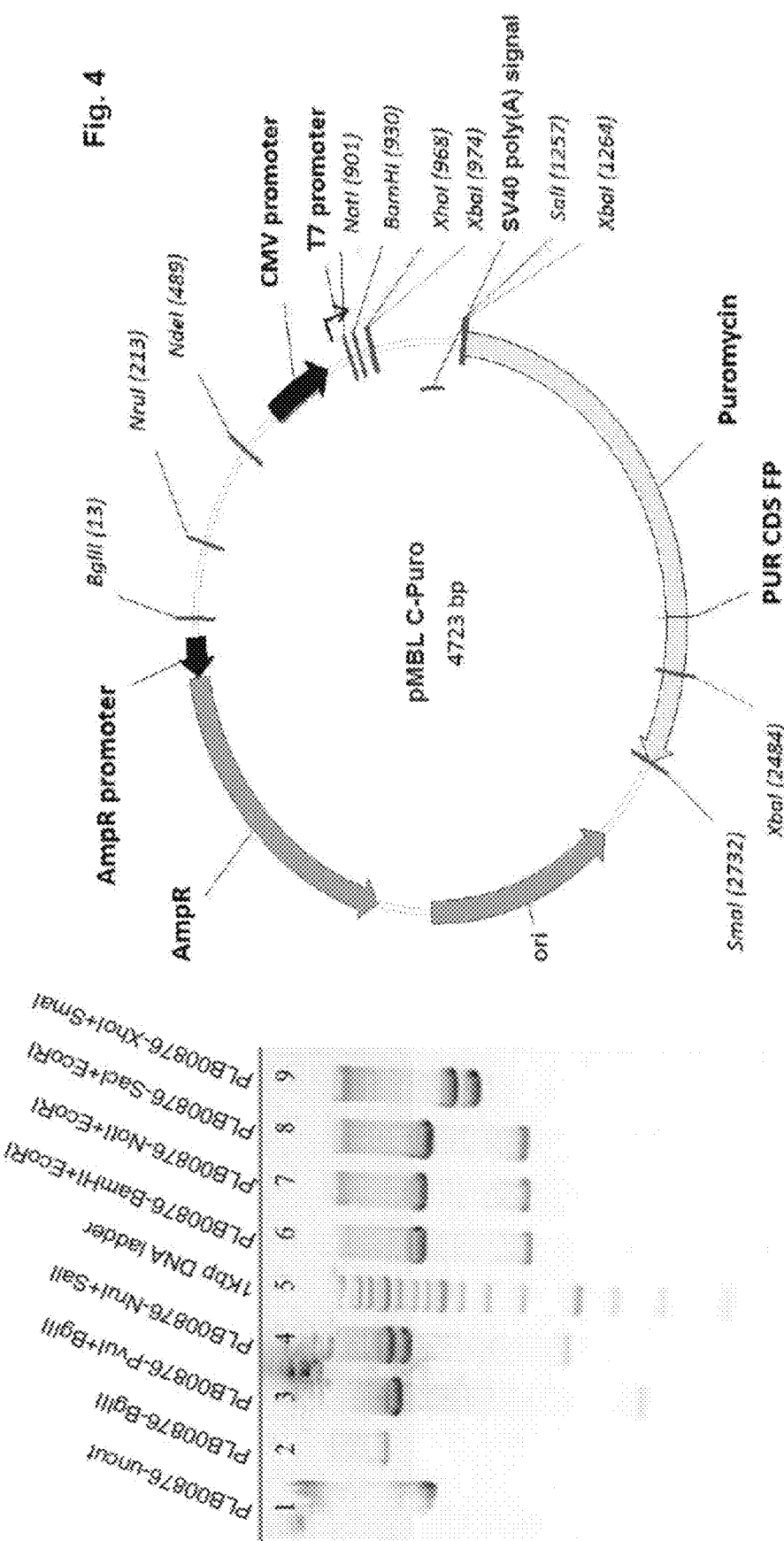
FIG. 4 is a vector map of pMBL C-Puro.
FIG. 5A depicts the gel electrophoretic restriction analysis of vector pMBL C-GS.

The plasmid stock was analysed by restriction digestion and subsequent agarose gel electrophoresis. FIG. 5A depicts the obtained gel.

Characterization of Vector pMBL CE-GS

The EASE fragment was obtained from Geneart (GA Fragment 3). The EASE element had been sub cloned upstream of CMV promoter at the BglII site, thereby obtaining vector pMBL C-GS. The EASE fragment was resuspended in 50 μL of sterile water to obtain a final concentration of 100 ng/μL.

1 μL was transformed to CCB00024 chemically competent cells.

A single colony obtained was streaked and the plasmid was isolated. The EASE fragment was released from the GA Fragment 3 by using the BglII+BamHI sites, and cloned in pMBL C-GS (PLB00876) at the BglII site. The resulting vector obtained is pMBL CE-GS.

Figure 5C:
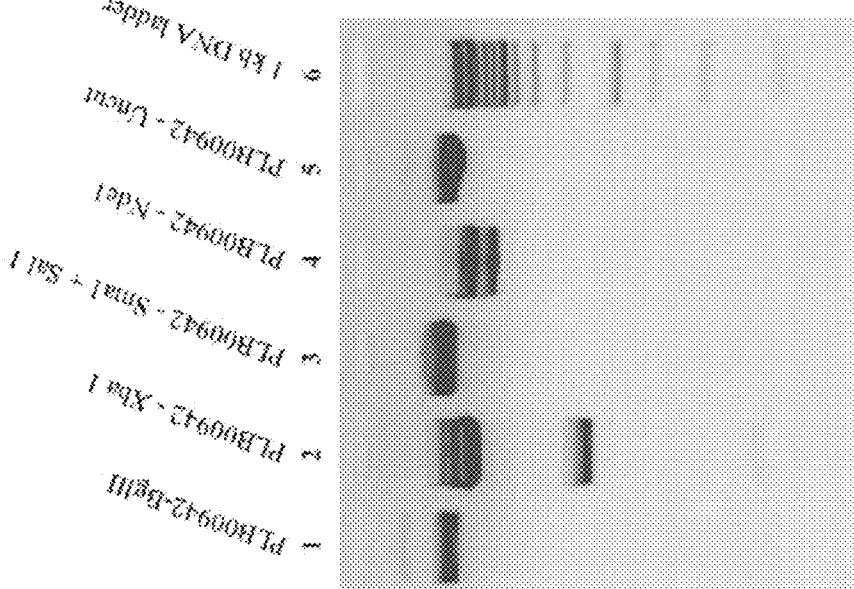
FIG. 5C depicts the gel electrophoretic restriction analysis of vector pMBL CE-Puro.
Figure 5B:
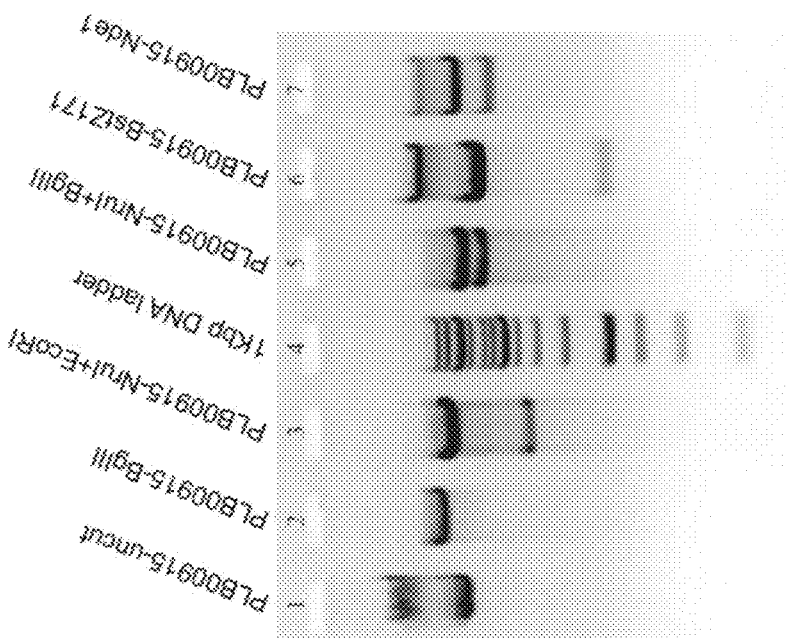
FIG. 5B depicts the gel electrophoretic restriction analysis of vector pMBL CE-GS.

The identity of vector pMBL CE-GS was analysed by restriction digestion and subsequent agarose gel electrophoresis. FIG. 5B depicts the obtained gel.

Characterization of Vector pMBL CE-Puro

The puromycin gene (GA Fragment 2) was obtained from Geneart. The EASE element had been sub cloned upstream of the CMV promoter at the BglII site, and the GS ORF had been replaced with a Puromycin selection marker for CHO at the SmaI/SalI sites, supra. The fragment was resuspended m 50 µL of sterile water to obtain a final concentration of 100 ng/µL.

1 µL was transformed to CCB00024 chemically competent cells. A single colony was streaked and the plasmid was isolated.

The puromycin gene from GA fragment 2 was cloned into the vector pMBL CE-GS at the SmaI+SalI site. The resulting vector obtained is the vector pMBL CE-Puro.

The identity of vector PMBL CE-Puro was analysed by restriction digestion and subsequent agarose gel electrophoresis. FIG. 5C depicts the obtained gel.

Characterization of Vector pMBL C-Puro

The puromycin gene (GA Fragment 2) was obtained from Geneart. The GS ORF had been replaced with a Puromycin selection marker for CHO at the SmaI/SalI sites, supra. The fragment was resuspended in 50 µL of sterile water to obtain a final concentration of 100 ng/µL.

1 µL was transformed to CCB00024/CHE chemically competent cells. A single colony. was streaked and the plasmid was isolated.

The puromycin fragment from GA fragment 2 was released by using SmaI+SalI sites and cloned into vector pMBL C-GS at the SmaI+SalI sites. The resulting vector obtained is the vector pMBL C-Puro.

Figures 5D, 6:
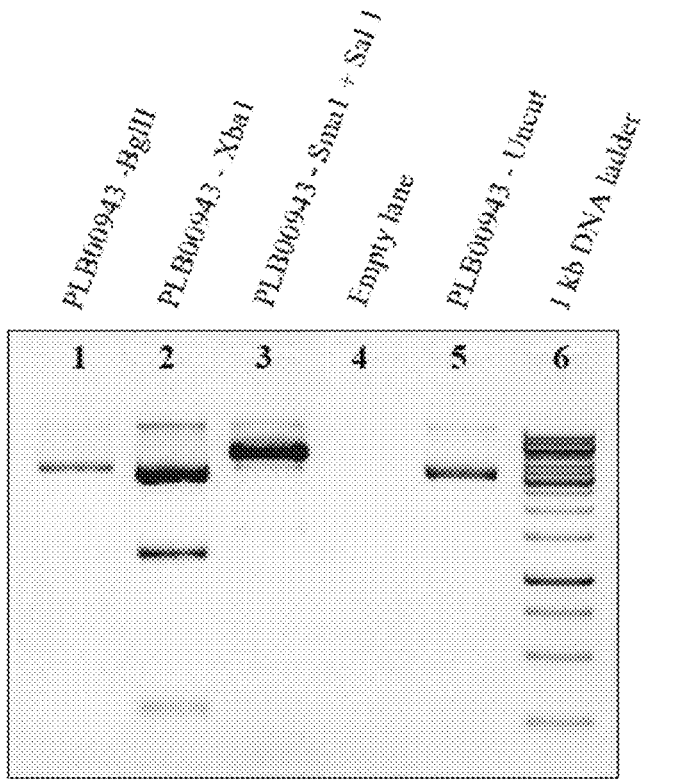
FIG. 5D depicts the gel electrophoretic restriction analysis of vector pMBL C-Puro.
FIG. 6 is a table providing an overview on the monoclonal antibodies expressed using vectors according to the disclosure.

The identity of vector PMBL C-Puro was analysed by restriction digestion and subsequent agarose gel electrophoresis. FIG. 5D depicts the obtained gel.

Vector Evaluation

The assembled vectors were further evaluated on the basis of their capability to drive heterologous gene expression in a CHO based cell line. As a start, pMBL CE-GS was selected for evaluation. The following constructs were created in DMBL CE-GS:

the expiCHO-S expression system manual. After a minimum of two passages post thaw, the cells were seeded for transfection at $3.5 \times 10^6$ cells/ml one day before transfection. On day 1 post seeding, the cell count was estimated and adjusted to $6.0 \times 10^6$ cells/ml by diluting with fresh, pre-warmed medium for each transfection. Transfection was carried out according to the expiCHO-S expression system manual. DNA was transfected at 1 µg/ml final concentration in culture. Expifectamine and feeds were added according to the manufacturer's protocol. Max titre protocol was followed for all transfections. Transfection flasks were cultivated at ~37° C. in an incubator with a humidified atmosphere of 8% $CO_2$ in air on an orbital shaker. VCD and viabilities were estimated on days, 0, 2, 5, 7, 9, and 12. Cultures were harvested when viability dropped below 50%.

Experiment 2:

Heavy chain and light chain of an anti-CTLA4 antibody (Bmab700) were cloned into the vectors pMBL CE-GS and pMBL C-GS at the XhoI-NotI site. The resulting constructs were evaluated in comparison to Bmab700-SSC/pCHO1.0 M (HC and LC cloned in two individual vectors and co-transfected) and Bmab700-DGC/pCHO1.0 (HC and LC cloned in a single vector). The four constructs were compared by transient gene expression.

Transient transfections were performed in co-transfection mode. All transfections were carried out by using the ExpiCHO™ Expression System (Cat. no. A29133 from Thermo Fisher Scientific Inc., Waltham, MA USA), a high-yield transient expression system based on suspension-adapted CHO cells. ExpiCHO-S cells were thawed according to the expiCHO-S expression system manual. After a minimum of two passages post thaw, the cells were seeded for transfection at $3.5 \times 10^6$ cells/ml one day before transfection. On day 1 post seeding, the cell count was estimated and adjusted to $6.0 \times 10^6$ cells/ml by diluting with fresh, pre-warmed medium for each transfection. Transfection was carried out as per expiCHO-S expression system manual. DNA was transfected at 1 µg/ml final concentration in culture. Expifectamine and feeds were added according to the manufacturer's protocol. Max titre protocol was followed for all transfections.

Transfection flasks were cultivated at ~37° C. incubator with a humidified atmosphere of 8% $CO_2$ in air on an orbital shaker. VCD and viabilities were estimated on days, 0, 2, 5, 7, 9, and 12. Cultures were harvested on day-15 and results

TABLE 3

| Constructs tested for vector evaluation | | | | | | |
|---|---|---|---|---|---|---|
| Experiment | Experiment 1 | Experiment 2 | | Experiment 3 | | |
| Construct tested | GFP/ pMBL CE-GS Transfection efficiency control | Bmab700/ pMBL CE-GS | Bmab700/ pMBL C-GS | Fmab25 | Fmab26 Fmab27 Fmab28 | |
| | | Titer comparision for Biosimilar mAb | | Titer comparision for fusion mAb | | |

Figure 7A:
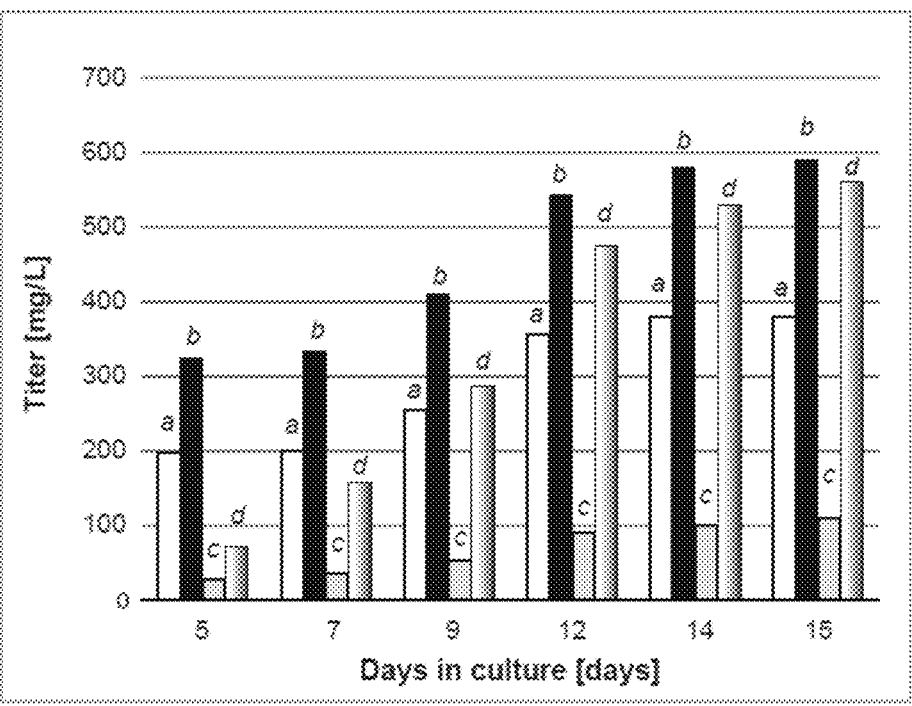
FIG. 7A depicts the titers of anti-CTLA4 antibody Bmab700 expressed using the vector pMBL CE-GS (a) and the vector pMBL C-GS (b), in comparison to the expression after co-transfection of HC and LC of the same anti-CTLA4 antibody in two individual pCHO 1.0 vectors (c) and expression using a single pCHO 1.0 vector, into which both HC and LC had been cloned (d).

Experiment 1:

GFP was cloned into the vector pMBL CE-GS at XhoI-NotI sites. This plasmid acts as a transfection efficiency control to evaluate pMBL CE-GS. The plasmid was evaluated by transient gene expression. Transient transfections were performed in co-transfection mode. All transfections were carried out by using the ExpiCHO™ Expression System (Cat. no. A29133 from Thermo Fisher Scientific Inc., Waltham, MA USA), which is a high-yield transient expression system based on suspension-adapted Chinese Hamster Ovary (CHO) cells. ExpiCHO-S cells were thawed as per are depicted in FIG. 7A. Culturing was carried out in shake flasks of 125 ml capacity, in which 25 ml running volume was used.

Results are depicted in FIG. 7A.

Figure 7B:
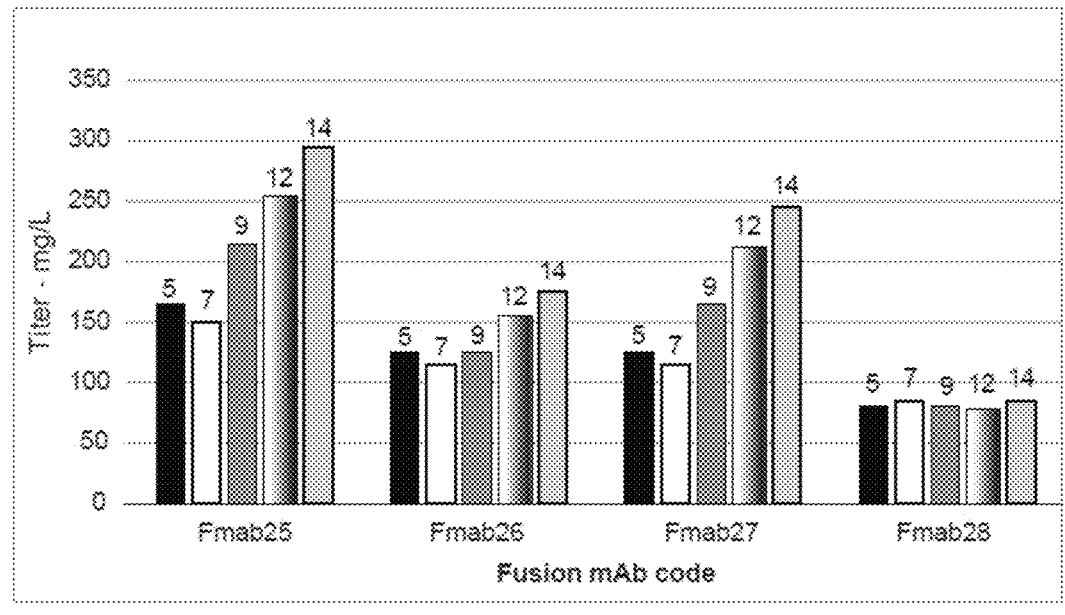
FIG. 7B depicts the titers of four different anti-CD20 fusion antibodies at days 5, 7, 9, 12 and 14 expressed using pMBL CE-GS. Both HC and LC had been cloned into the vector pMBL CE-GS at the XhoI-NotI sites. Days are indicated above the bars. Transient transfections were performed in co-transfection mode. All transfections were carried out by using The ExpiCHO™ Expression System (Cat. no. A29133 from Thermo Fisher Scientific Inc., Waltham, MA USA), this is a high-yield transient expression system based on suspension-adapted Chinese Hamster Ovary (CHO) cells. ExpiCHO-S cells were thawed as per the expiCHO-S expression system manual. After a minimum of 2 passages post thaw, the cells were seeded for transfection at $3.5 \times 10^6$ cells/ml one day before transfection. On day 1 post seeding, the cell count was estimated and adjusted to $6.0 \times 10^6$ cells/ml by diluting with fresh, prewarmed medium for each transfection. Transfection was carried out as per expiCHO-S expression system manual. DNA was transfected at 1 µg/ml final concentration in culture. Expifectamine and feeds were added as per manufacturer's protocol. Max titre protocol was followed for all transfections. Transfection flasks were cultivated at 37° C. incubator with a humidified atmosphere of 8% $CO_2$ in air on an orbital shaker. VCD and viabilities were estimated on days, 0, 2, 5, 7, 9, and 12. Cultures were harvested when viability dropped below 50% or on D-12.
Figure 8A:
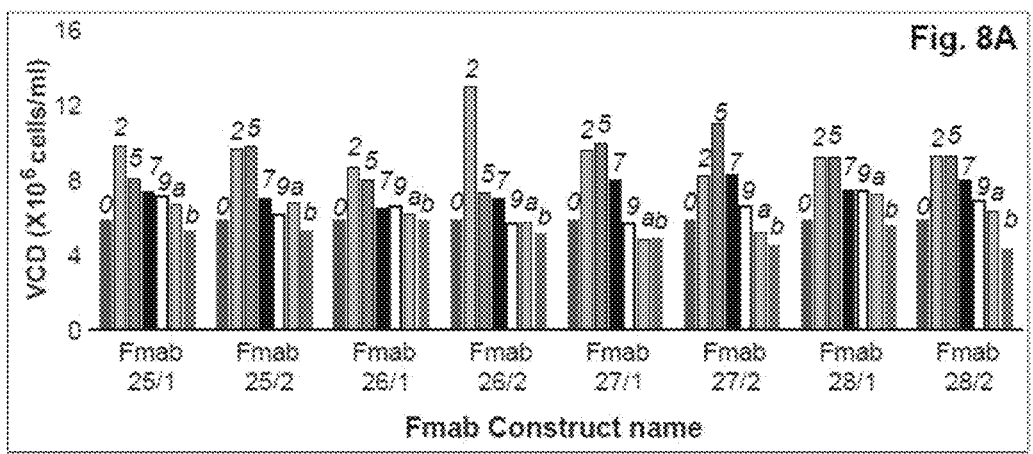
FIG. 8A depicts the time course of the viable cell density, and FIG. 8B of the cell viability in % of CHO cells expressing an anti-CD20 HC-C-TGFβRII fusion antibody, (Fmab25/1 and Fmab25/2), an anti-CD20 LC-C-TGFβRII fusion antibody (Fmab26/1 and Fmab26/2), an anti-CD20 HC-N-TGFβRII fusion antibody (Fmab27/1 and Fmab27/2), and a further anti-CD20 LC-N-TGFβRII fusion antibody (Fmab28/1 and Fmab28/2), transiently expressed using the vector pMBL CE-GS.
Figure 8B:
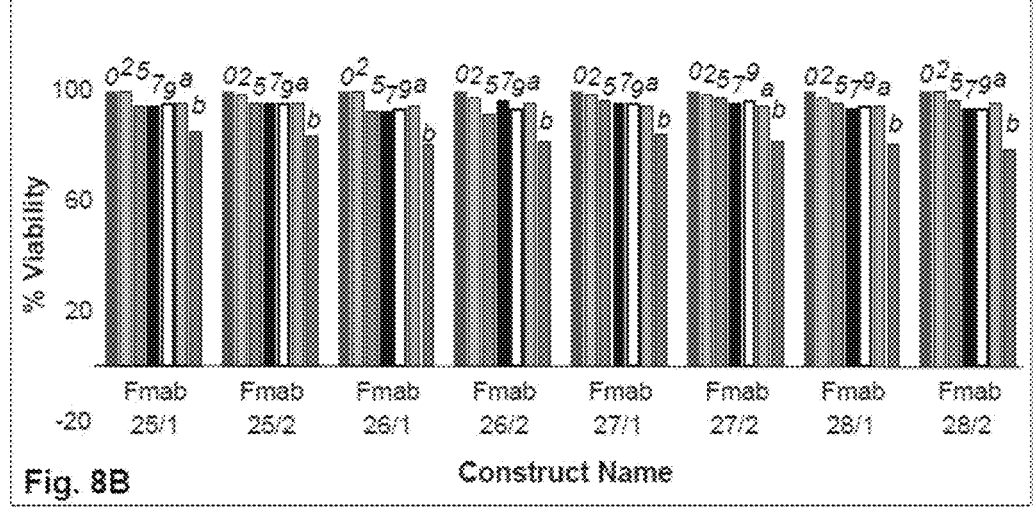
FIG. 8C depicts the time course of the titer of product produced. Measurements were done on day 0, day 2, day 5, day 7, day 9, day 12 and day 14. Numbers on bars indicate the respective day of culture, a=day 12, b=day 14.
FIG. 8D shows the harvest titer of product produced on day 14. Harvest Titer analysis was done based on HPLC method for Day-14 samples. Transient expression studies were conducted as described in paragraph [0032].
Figure 8C:
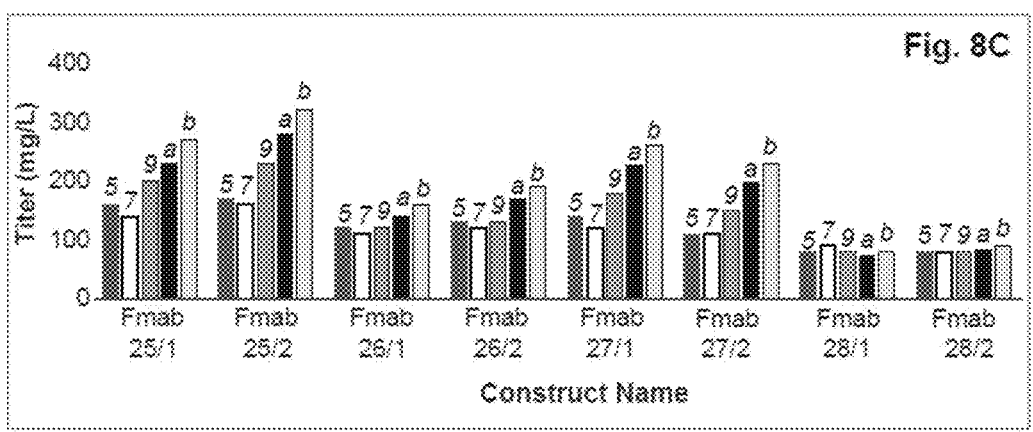
Figure 8D:
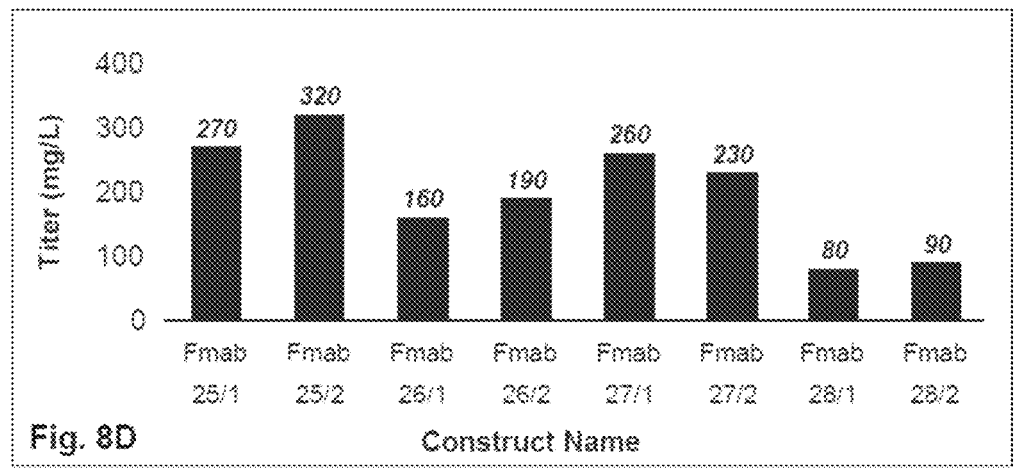
Figure 9A:
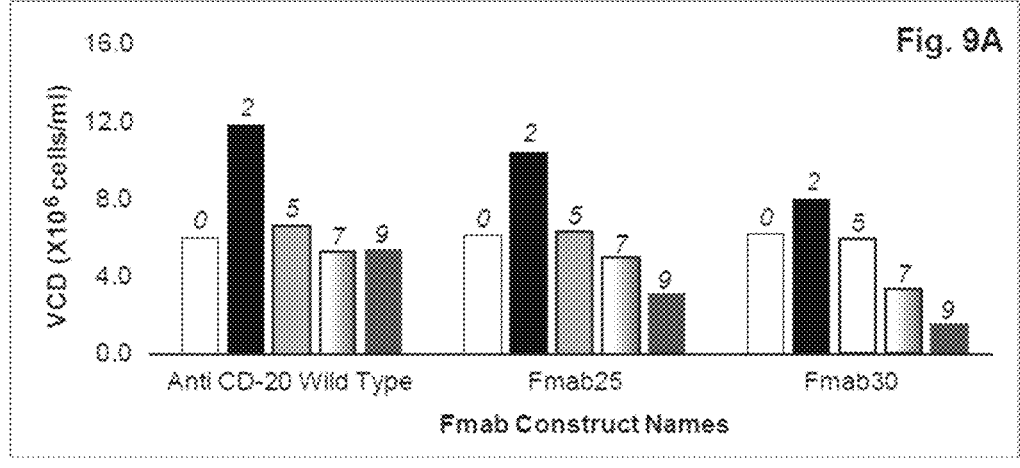
FIG. 9A depicts the time course of the viable cell density, and FIG. 9B of the cell viability in % of CHO cells expressing an anti CD-20 wild type antibody, an anti-CD20 HC-C-TGFβRII fusion antibody (Fmab25), and an anti- CD20 TIM3 LC-C-Terminus fusion antibody (Fmab30). Growth profiles were monitored on day 0, day 2, day 5, day 7 and day 9. Numbers on bars indicate the respective day of culture.
Figure 9B:
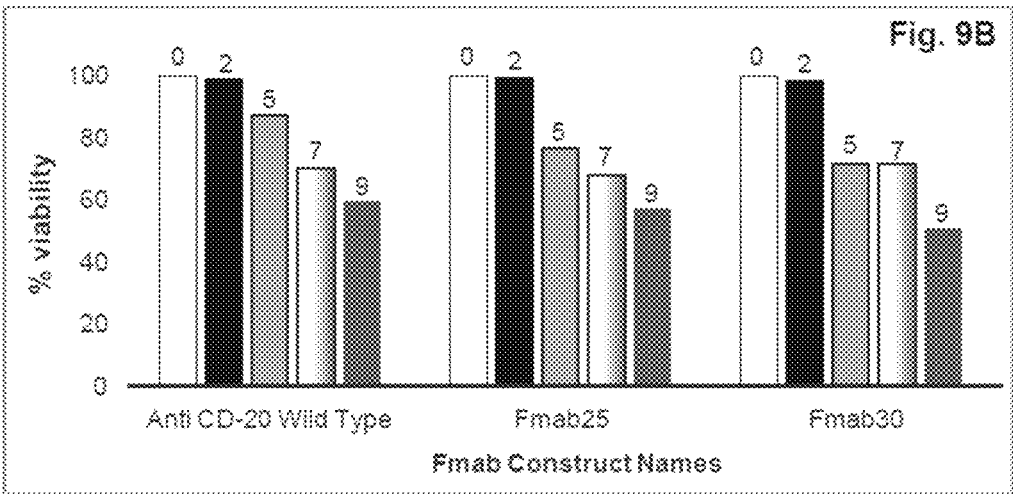
FIG. 9C depicts the time course of the titer of product produced. Measurements were done on day 5, day 7 and day 9. Numbers on bars indicate the respective day of culture.
FIG. 9D shows the harvest titer of product produced on day 9. Numbers on bars indicate the titer obtained. Analysis was based on HPLC.
Figure 9C:
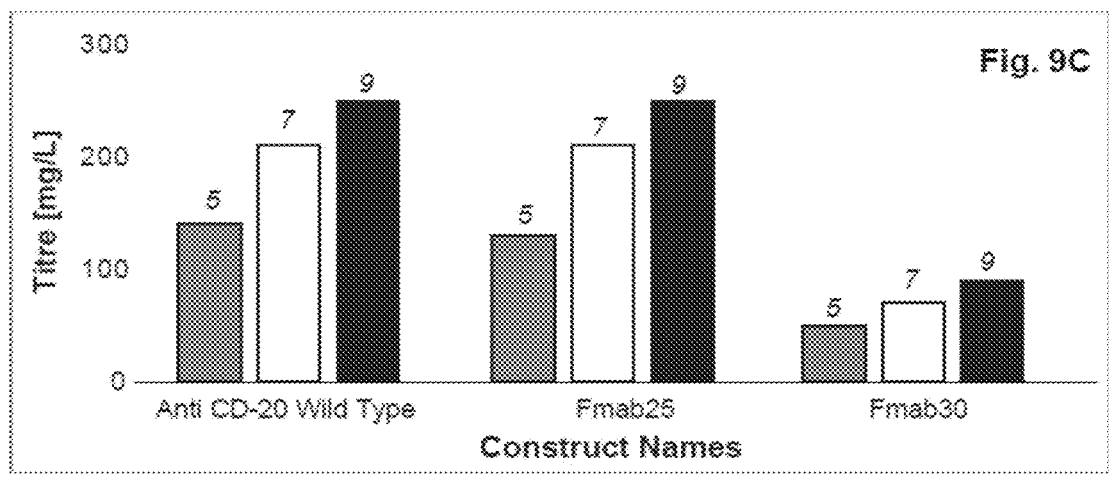
Figure 9D:
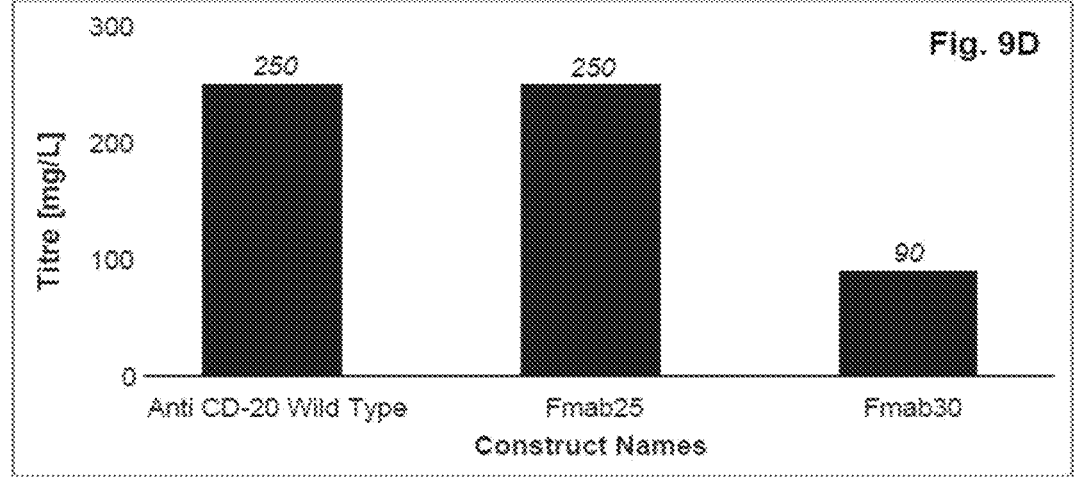
Figure 10A:
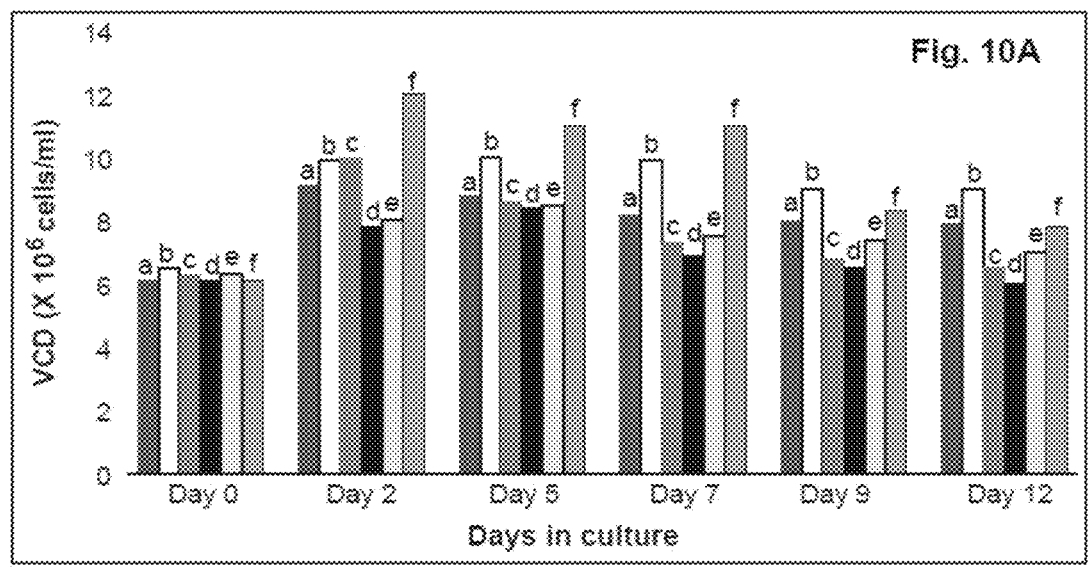
FIG. 10A depicts the time course of the viable cell density, and FIG. 10B of the cell viability in % of CHO cells expressing an anti-PDL-1 antibody. Measurements were done on day 0, day 2, day 5, day 7, day 9 and day 12. Letters on bars indicate the respective antibody chain expressed: a-c: Atezolizumab, d-f: anti-PDL-1 antibody.
Figure 10B:
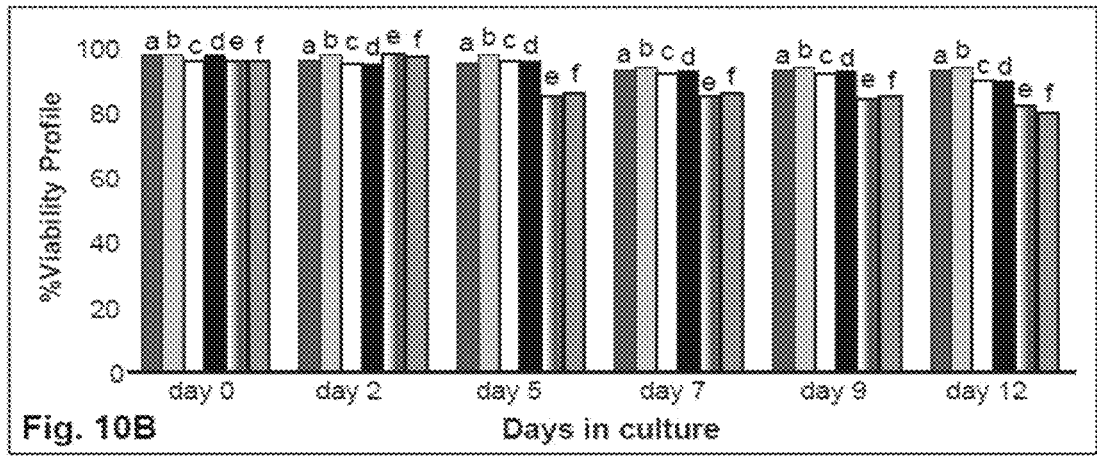
FIG. 10C shows the harvest titer of product produced on day 14. Numbers on bars indicate the titer obtained. Analysis was based on HPLC.
Figure 10C:
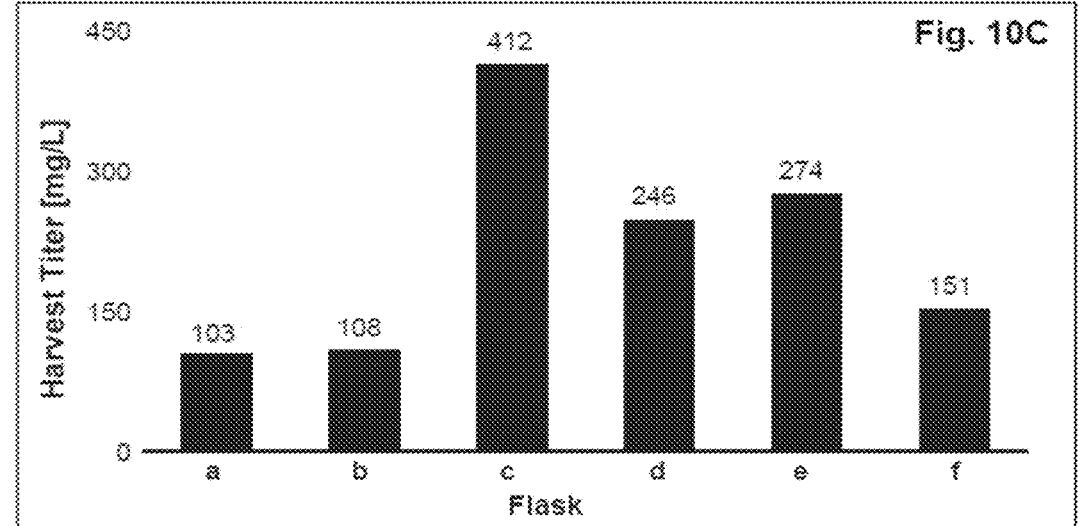
Figure 11A:
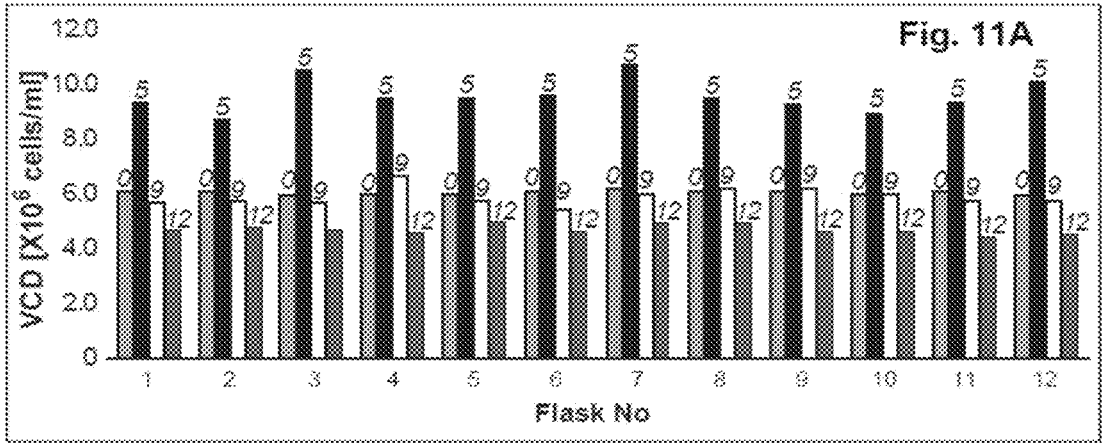
FIG. 11A depicts the time course of the viable cell density, and FIG. 11B of the cell viability in % CHO cells expressing a further anti-PDL-1 antibody. Measurements were done on day 0, day 5, day 9 and day 12. Numbers on bars indicate the respective day of culture.
Figure 11B:
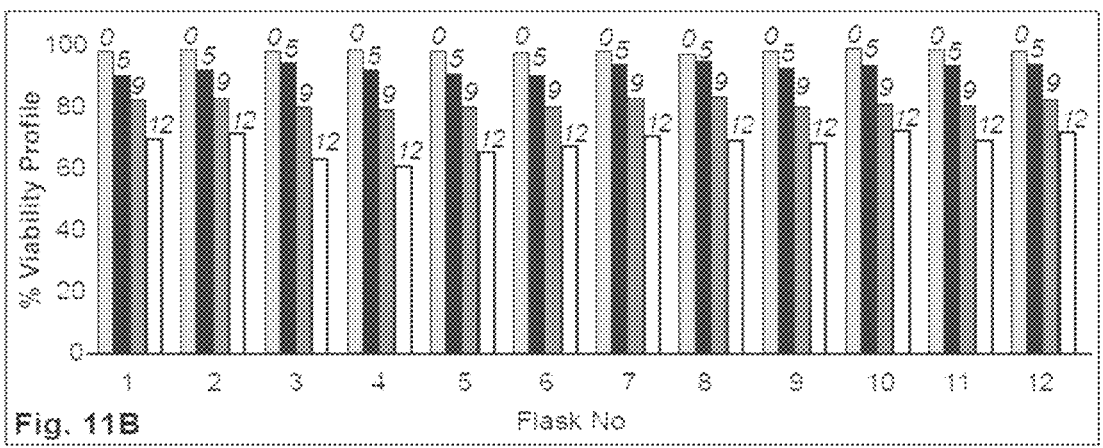
FIG. 11C depicts the time course of the titer of product produced. Measurements were done on day 9 and day 12. Numbers on bars indicate the respective day of culture.
FIG. 11D shows the harvest titer of product produced on day 12. Numbers on bars indicate the titer obtained. Analysis was based on HPLC.
Figure 11C:
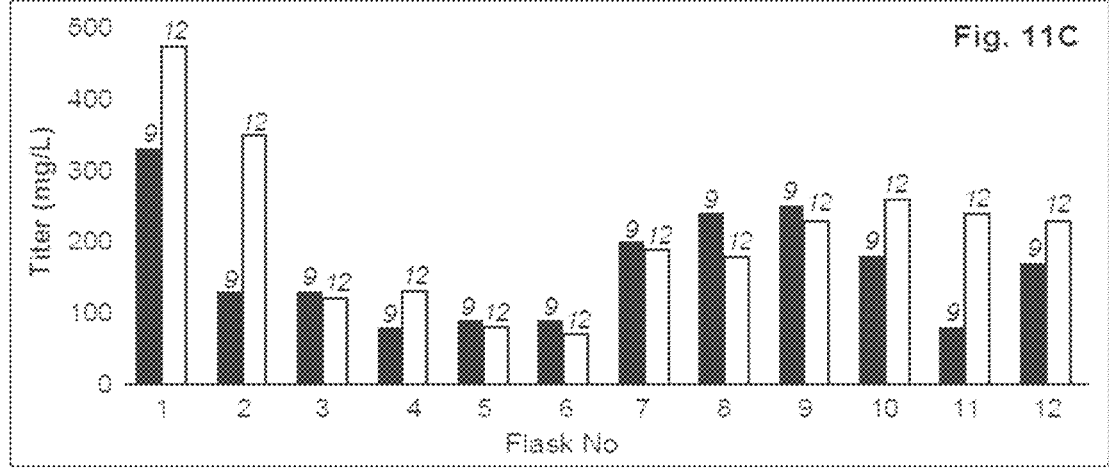
Figure 11D:
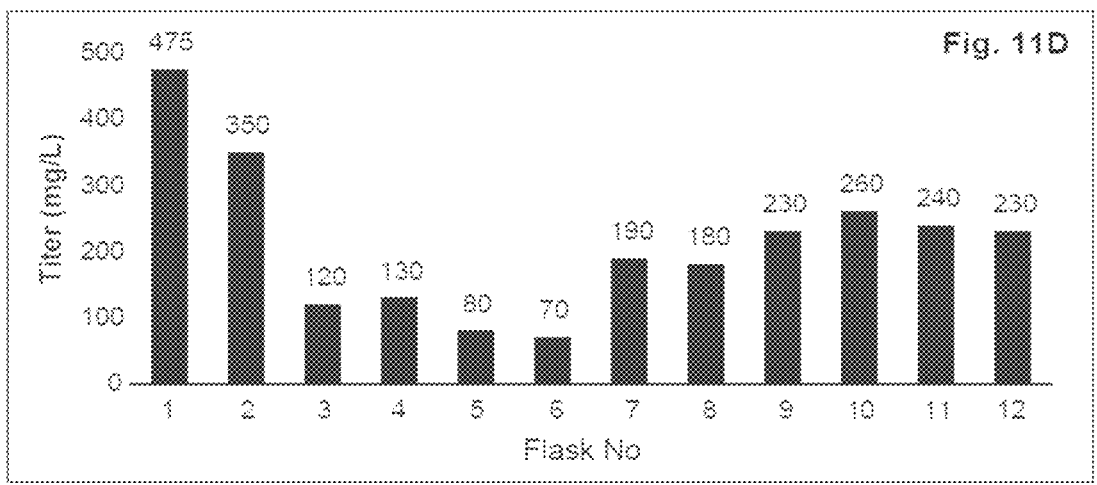
Figure 12A:
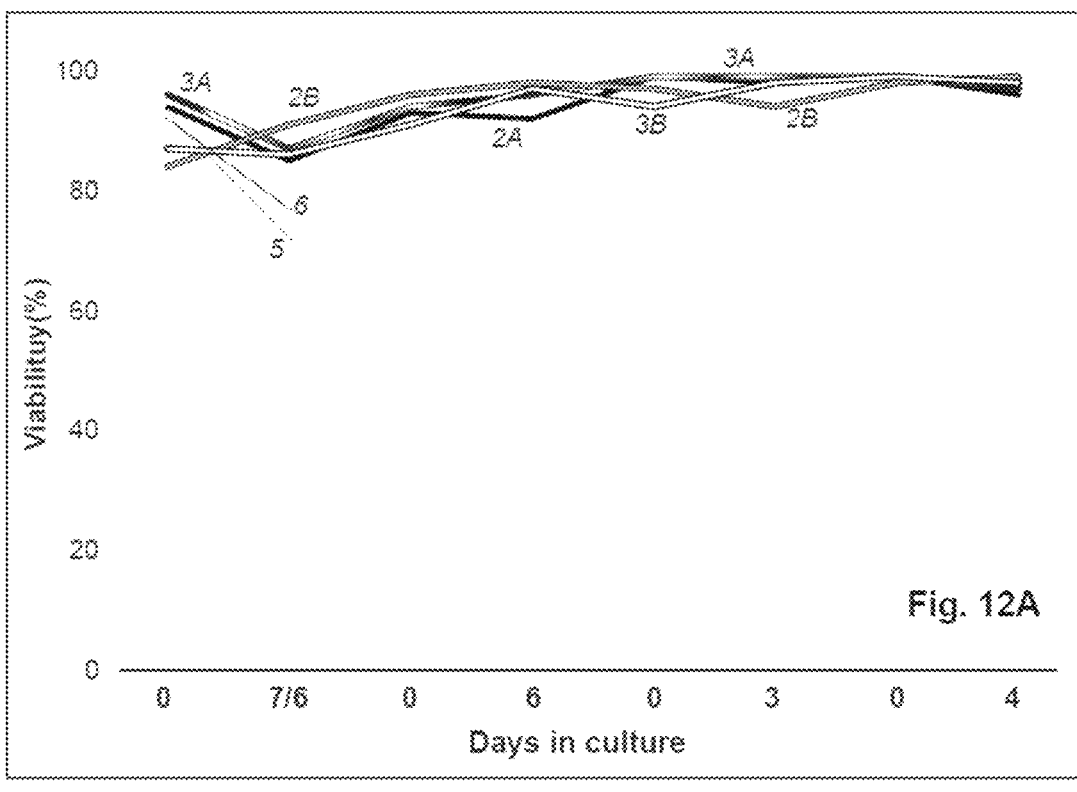
FIG. 12A shows the viability in six flasks in % and FIG. 12B the viable cell density during the selection phase in the absence of glutamine. Flasks 2A, 2B, 3A and 3B contained CHO cells of different CHO-S GS knock out hosts, stably transfected with pMBL CE-GS by means of electroporation, and Flasks 5 and 6 represent mock cell controls containing CHO cells electroporated with no DNA for C12-1 and C#26-2 respectively. Flasks 2A and 2B and flasks 3A and 3B were replicate flasks of the same cell lines, respectively. pMBL CE-GS encoded etanacerpt, a fusion protein of the extracellular ligand-binding domain of the p75 TNF receptor and the human Fc portion of IgG1. Each day 0 was the day of seeding. Days 7/6, 6, 3 and 4, respectively were days in selection.
Figure 12B:
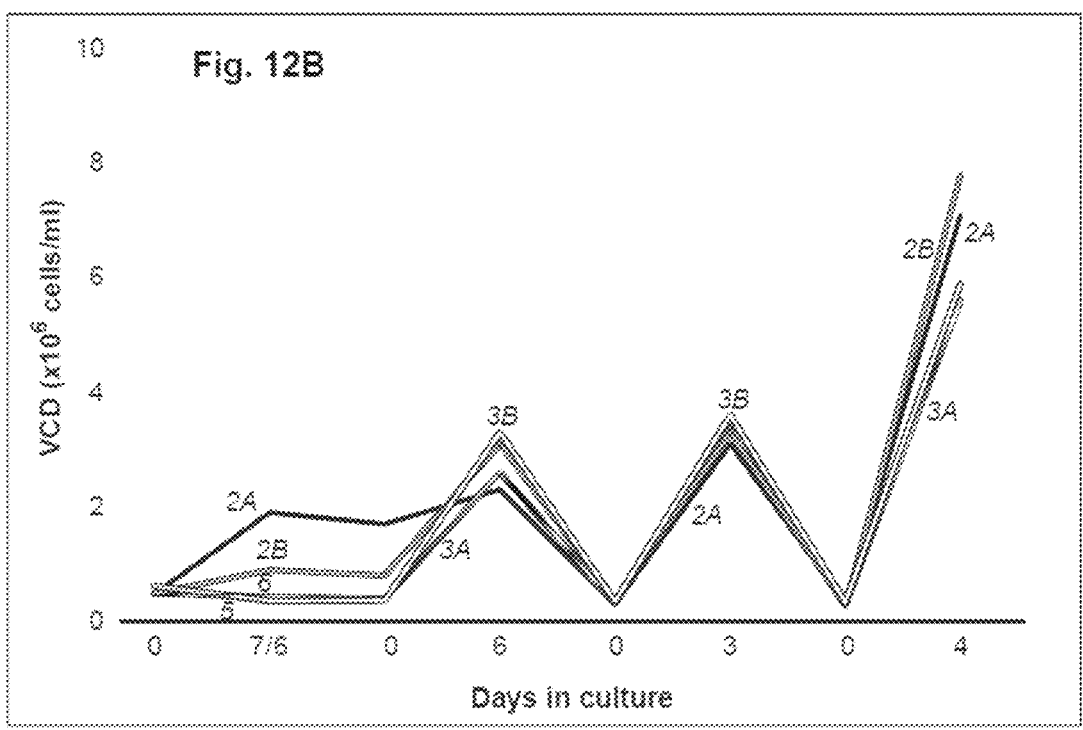
Figure 13A:
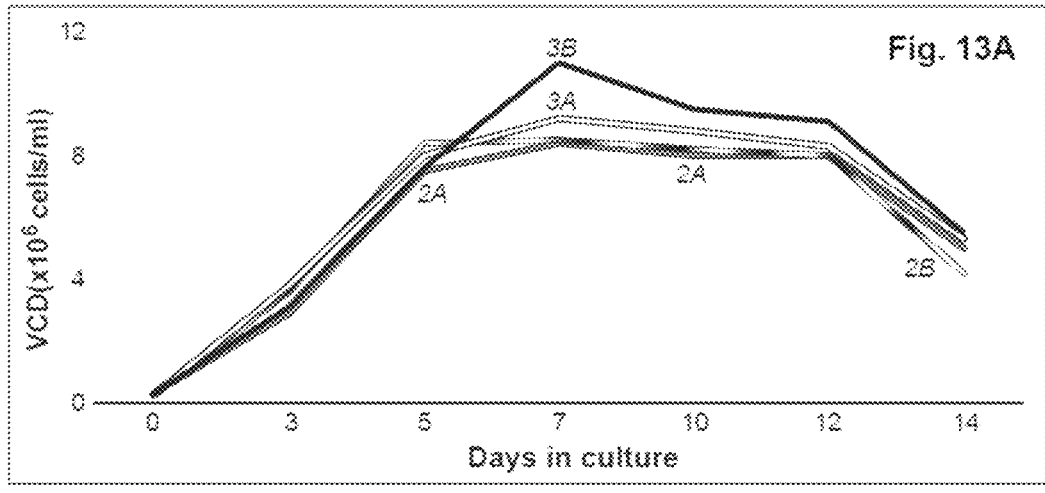
FIG. 13A depicts the time course of the viable cell density, and FIG. 13B of the cell viability in % of CHO cells of the same flasks as in FIGS. 12A and B, stably expressing etanacerpt. Glucose was used as feed under simple fed batch culture, data were collected at passage No 5.
Figure 13B:
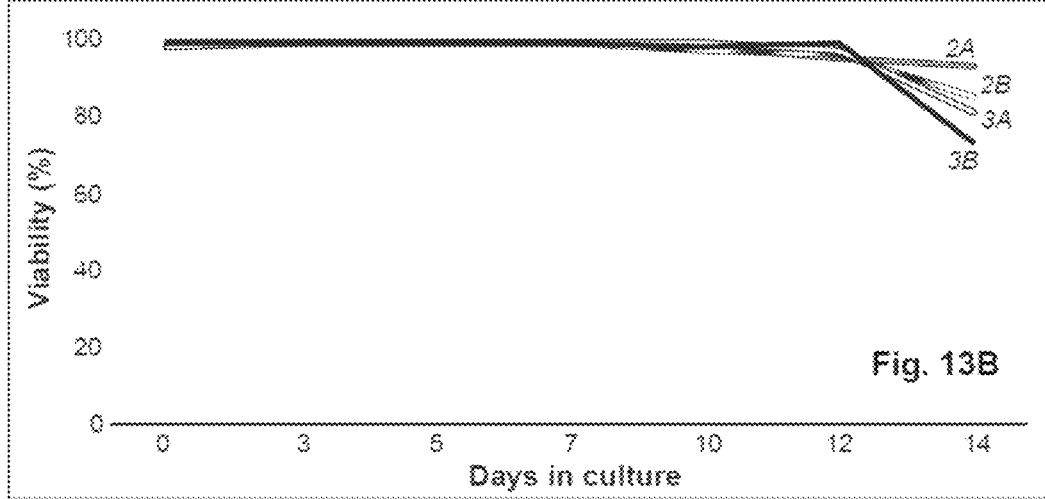
FIG. 13C depicts the time course of the titer of product produced. Measurements were done on day 5, day 7, day 10 and day 14. Numbers on bars indicate the respective day of culture.
FIG. 13D shows the harvest titer of product produced on day 14. Titer were estimated by using HPLC.
Figure 13C:
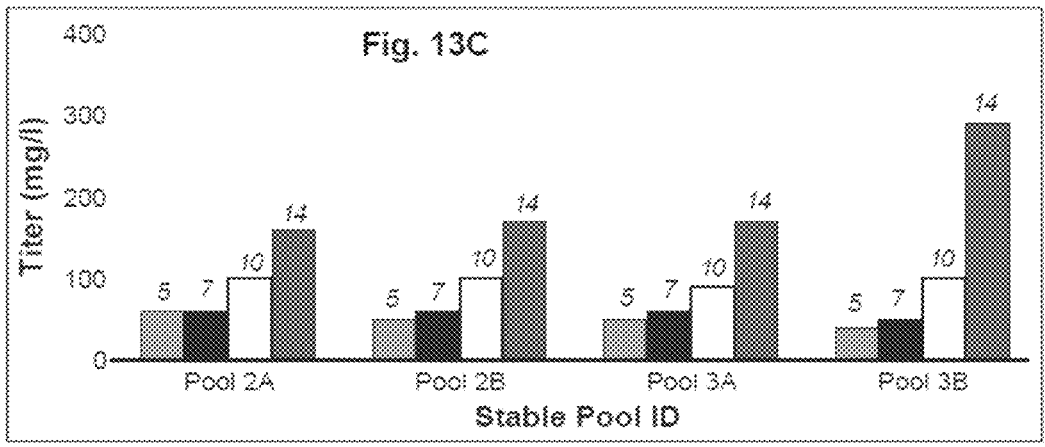
Figure 13D:
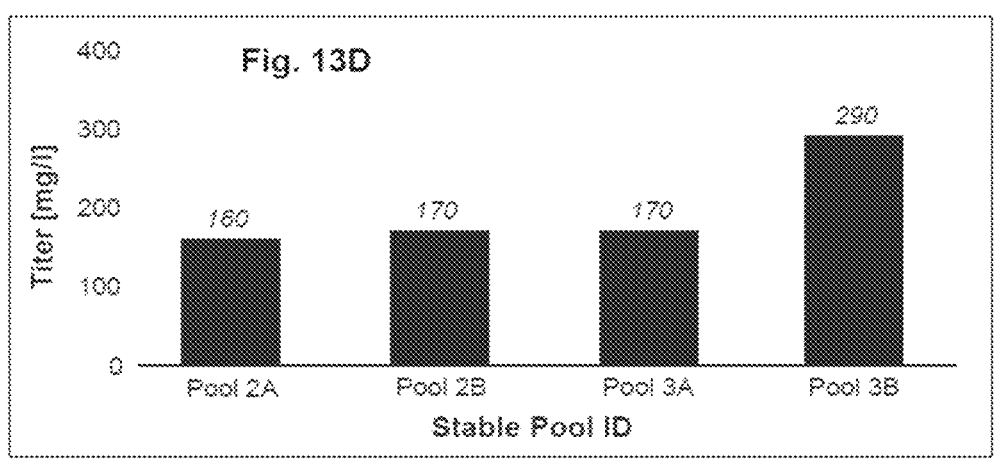
Figure 14A:
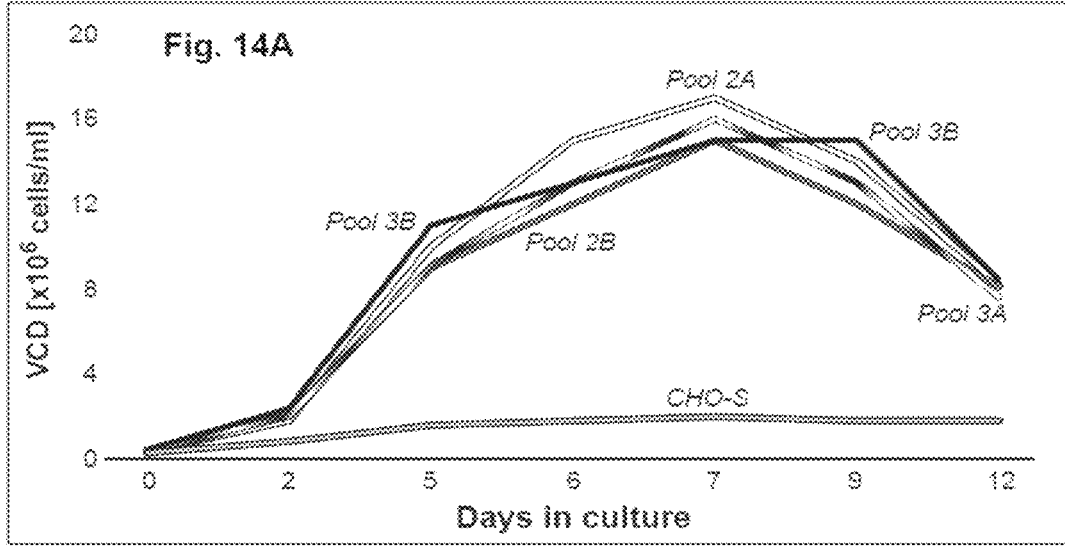
FIG. 14A depicts the time course of the viable cell density, and FIG. 14B of the cell viability in % of CHO cells of the same pools as in FIG. 12A, B and FIG. 13, stably expressing etanacerpt. CB4 (Cell Boost-4 from Hyclone, GE Healthcare Life Sciences) and EFC (Efficient feed C from Thermo Fisher Scientific Inc., Waltham, MA USA) were used as feeds under fed batch culture, data were collected at passage No 7.
Figure 14B:
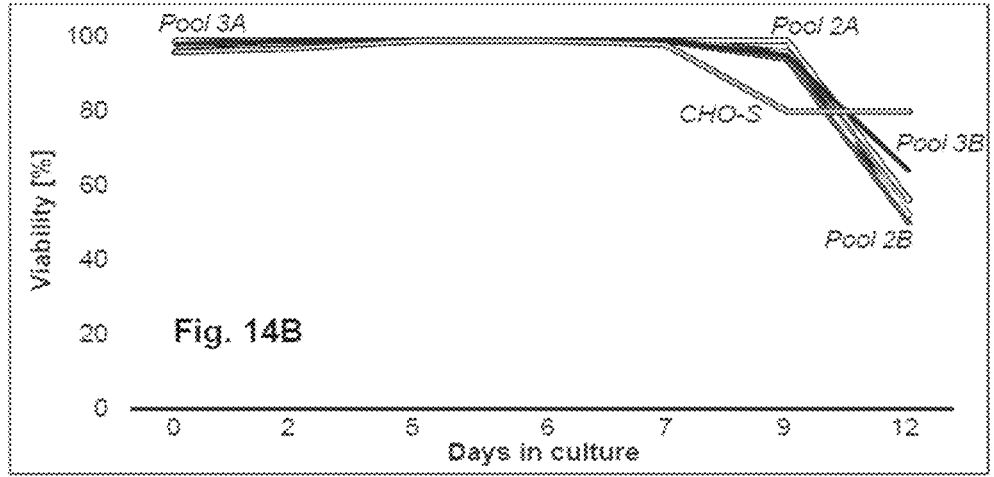
FIG. 14C depicts the time course of the titer of product produced. Measurements were done on day 7 and day 12. Numbers on bars indicate the respective day of culture.
FIG. 14D shows the harvest titer of product produced on day 12.
Figure 14C:
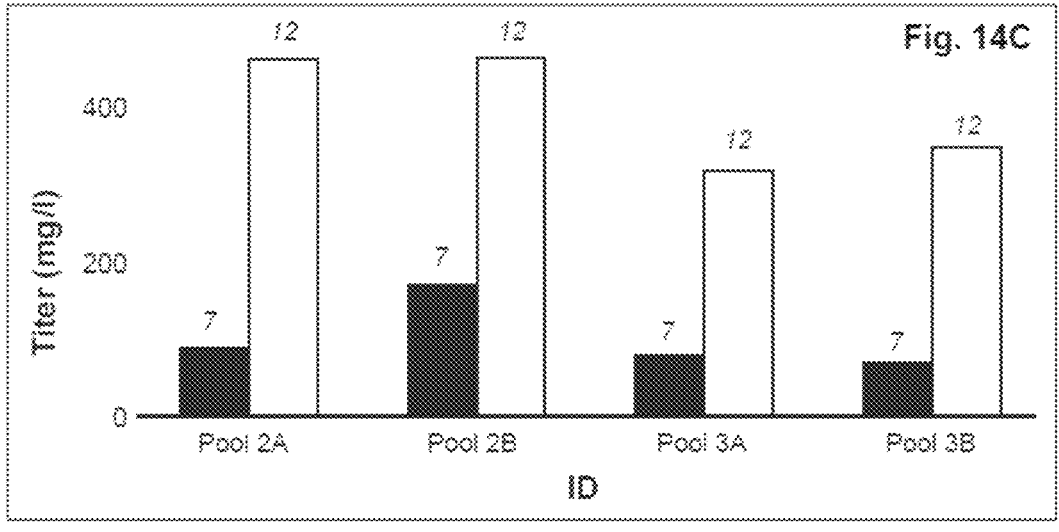
Figure 14D:
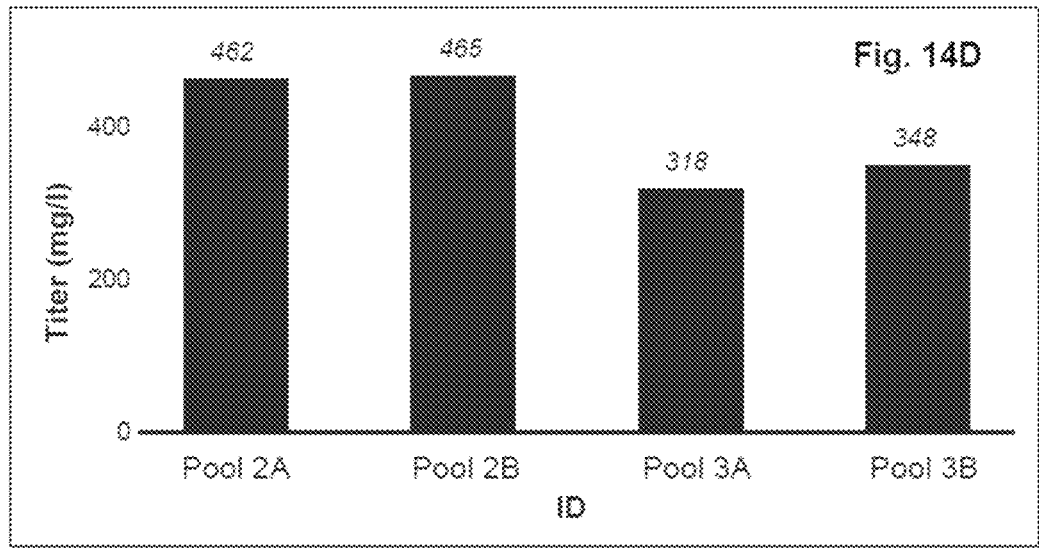
Figure 15:
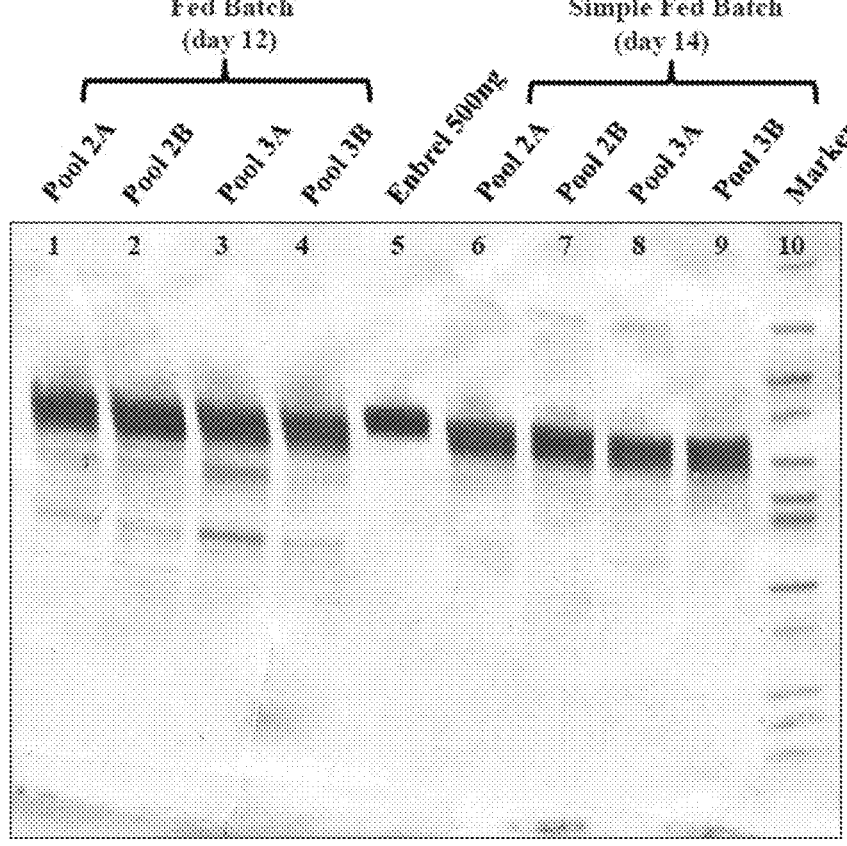
FIG. 15 depicts a Western blot analysis of harvest samples for which data are provided in FIG. 13 and FIG. 14. Non-purified harvest supernatant from fed batch (cf FIG. 14) and simple fed batch (cf FIG. 13) was analysed.

Experiment 3:

HC and LC of anti-CD20 fusion mabs were cloned into the vector pMBL CE-GS at the XhoI-NotI site. The resulting constructs were evaluated for titer analysis by transient gene expression. Transient transfections were performed in co-transfection mode. All transfections were carried out by using The ExpiCHO™ Expression System (Cat. no. A29133 from Thermo Fisher Scientific Inc., Waltham, MA USA), a high-yield transient expression system based on suspension-adapted CHO cells. ExpiCHO-S cells were thawed as per the expiCHO-S expression system manual. After a minimum of 2 passages post thaw, the cells were seeded for transfection at 3.5×10⁶ cells/ml one day before transfection. On day 1 post seeding, the cell count was estimated and adjusted to 6.0×10⁶ cells/ml by diluting with fresh, pre-warmed medium for each transfection. Transfection was carried out as per expiCHO-S expression system manual. DNA was transfected at 1 µg/ml final concentration in culture. Expifectamine and feeds were added as per manufacturer's protocol. The max titre protocol was followed for all transfections. Transfection flasks were cultivated at ~37° C. incubator with a humidified atmosphere of 8% $CO_2$ in air on an orbital shaker. VCD and viabilities were estimated on days, 0, 2, 5, 7, 9, and 12. Cultures were harvested on day 14. Results are depicted in FIG. 7B.

---

We claim:

1. An expression vector for mammalian cells, comprising
    (a) a first selection cassette comprising a nucleotide sequence encoding a glutamine synthetase as an eukaryotic selection marker, operably linked to a 3-phosphoglycerate kinase (PGK) promoter and a polyadenylation (pA) signal;
    (b) a second selection cassette comprising a nucleotide sequence encoding an enzyme that confers resistance against an antibiotic to a bacterial host as a bacterial selection marker, operably linked to a suitable promoter;
    (c) an expression cassette for a target polypeptide, comprising an insertion site for inserting a nucleotide sequence encoding the target polypeptide, operably linked to a cytomegalovirus (CMV) promoter and a pA signal;
    (d) a bacterial origin of replication; and
    (e) an expression augmenting sequence element (EASE).

2. The expression vector of claim 1, wherein the antibiotic against which the bacterial selection marker confers resistance is Ampicillin, and wherein the enzyme that confers resistance against Ampicillin to a bacterial host is beta-lactamase.

3. The expression vector of claim 1, wherein the bacterial origin of replication is a pUC origin of replication.

4. The expression vector of claim 1, wherein the nucleotide sequence encoding the glutamine synthetase is of at least 90% identity to SEQ ID NO: 3, or wherein the glutamine synthetase is a mammalian glutamine synthetase.

5. The expression vector of claim 1, wherein the glutamine synthetase has an amino acid sequence of at least 96% identity to SEQ ID NO: 5.

6. The expression vector of claim 1, wherein the PGK promoter has a sequence of at least 98% identity to SEQ ID NO: 2, and/or wherein the glutamine synthetase is a CHO glutamine synthetase having at least 97% identity to SEQ ID NO: 5.

7. The expression vector of claim 1, wherein the pA signal is a simian virus 40 pA signal.

8. A recombinant CHO or NS0 host cell, comprising the expression vector of claim 1.

9. A method of producing a target polypeptide, the method comprising culturing the recombinant CHO or NS0 host cell of claim 8 under conditions suitable for expressing a heterologous target polypeptide, wherein the expression cassette comprises a nucleotide sequence encoding the target polypeptide inserted at the insertion site.

10. The method of claim 9, wherein the target polypeptide comprises an antibody or a fragment thereof.

* * * * *

SEQUENCE LISTING

```
<160> NUMBER OF SEQ ID NOS: 16

<210> SEQ ID NO 1
<211> LENGTH: 1624
<212> TYPE: DNA
<213> ORGANISM: Artificial Sequence
<220> FEATURE:
<223> OTHER INFORMATION: CHO glutamine synthetase linked to a PGK
      promoter

<400> SEQUENCE: 1
gggtagggga ggcgcttttc ccaaggcagt ctggagcatg cgctttagca gccccgctgg      60
gcacttggcg ctacacaagt ggcctctggc ctcgcacaca ttccacatcc accggtaggc     120
gccaaccggc tccgttcttt ggtggcccct tcgcgccacc ttctactcct cccctagtca     180
ggaagttccc ccccgccccg cagctcgcgt cgtgcaggac gtgacaaatg gaagtagcac     240
gtctcactag tctcgtgcag atggacagca ccgctgagca atggaagcgg gtaggccttt     300
ggggcagcgg ccaatagcag ctttgctcct tcgctttctg ggctcagagg ctgggaaggg     360
gtgggtccgg gggcgggctc aggggcgggc tcaggggcgg ggcgggcgcc cgaaggtcct     420
ccggaggccc ggcattctgc acgcttcaaa agcgcacgtc tgccgcgctg ttctcctctt     480
cctcatctcc gggcctttct cgatggccac ctcagcaagt tcccacttga acaaaaacat     540
caagcaaatg tacttgtgcc tgccccaggg tgagaaagtc caagccatgt atatctgggt     600
tgatggtact ggagaaggac tgcgctgcaa aacccgcacc ctggactgtg agcccaagtg     660
tgtagaagag ttacctgagt ggaattttga tggctctagt acctttcagt ctgagggctc     720
caacagtgac atgtatctca gccctgttgc catgtttcgg gacccctttcc gcagagatcc     780 caacaagctg gtgttctgtg aagttttcaa gtacaaccgg aagcctgcag agaccaattt     840
aaggcactcg tgtaaacgga taatggacat ggtgagcaac cagcacccct ggtttggaat     900
ggaacaggag tatactctga tgggaacaga tgggcaccct tttggttggc cttccaatgg     960
ctttcctggg ccccaaggtc cgtattactg tggtgtgggc gcagacaaag cctatggcag    1020
ggatatcgtg gaggctcact accgcgcctg cttgtatgct ggggtcaaga ttacaggaac    1080
aaatgctgag gtcatgcctg cccagtggga attccaaata ggaccctgtg aaggaatccg    1140
catgggagat catctctggg tggcccgttt catcttgcat cgagtatgtg aagactttgg    1200
ggtaatagca acctttgacc ccaagcccat tcctgggaac tggaatggtg caggctgcca    1260
taccaacttt agcaccaagg ccatgcggga ggagaatggt ctgaagcaca tcgaggaggc    1320
catcgagaaa ctaagcaagc ggcaccggta ccacattcga gcctacgatc caaggggggg    1380
cctggacaat gcccgtcgtc tgactgggtt ccacgaaacg tccaacatca cgactttttc    1440
tgctggtgtc gccaatcgca gtgccagcat ccgcattccc cggactgtcg gccaggagaa    1500
```

-continued

```
gaaaggttac tttgaagacc gccgcccctc tgccaattgt gacccctttg cagtgacaga      1560
agccatcgtc cgcacatgcc ttctcaatga gactggcgac gagcccttcc aatacaaaaa      1620
ctaa                                                                   1624
```

```
<210> SEQ ID NO 2
<211> LENGTH: 496
<212> TYPE: DNA
<213> ORGANISM: Artificial Sequence
<220> FEATURE:
<223> OTHER INFORMATION: PGK promoter

<400> SEQUENCE: 2
gggtagggga ggcgcttttc ccaaggcagt ctggagcatg cgctttagca gccccgctgg       60
gcacttggcg ctacacaagt ggcctctggc ctcgcacaca ttccacatcc accggtaggc      120
gccaaccggc tccgttcttt ggtggcccct tcgcgccacc ttctactcct cccctagtca      180
ggaagttccc ccccgccccg cagctcgcgt cgtgcaggac gtgacaaatg gaagtagcac      240
gtctcactag tctcgtgcag atggacagca ccgctgagca atggaagcgg gtaggccttt      300
ggggcagcgg ccaatagcag ctttgctcct tcgctttctg ggctcagagg ctgggaaggg      360
gtgggtccgg gggcgggctc aggggcgggc tcaggggcgg ggcgggcgcc cgaaggtcct      420
ccggaggccc ggcattctgc acgcttcaaa agcgcacgtc tgccgcgctg ttctcctctt      480
cctcatctcc gggcct                                                     496
```

```
<210> SEQ ID NO 3
<211> LENGTH: 1122
<212> TYPE: DNA
<213> ORGANISM: Artificial Sequence
<220> FEATURE:
<223> OTHER INFORMATION: GS ORF

<400> SEQUENCE: 3
atggccacct cagcaagttc ccacttgaac aaaaacatca agcaaatgta cttgtgcctg       60 cccccagggtg agaaagtcca agccatgtat atctgggttg atggtactgg agaaggactg      120
cgctgcaaaa cccgcaccct ggactgtgag cccaagtgtg tagaagagtt acctgagtgg      180
aattttgatg gctctagtac ctttcagtct gagggctcca acagtgacat gtatctcagc      240
cctgttgcca tgtttcggga ccccttccgc agagatccca caagctggt gttctgtgaa      300 gtttttcaagt acaaccggaa gcctgcagag accaatttaa ggcactcgtg taaacggata      360
atggacatgg tgagcaacca gcacccctgg tttggaatgg aacaggagta tactctgatg      420
ggaacagatg ggcacccttt tggttggcct tccaatggct ttcctgggcc ccaaggtccg      480
tattactgtg gtgtgggcgc agacaaagcc tatggcaggg atatcgtgga ggctcactac      540
cgcgcctgct tgtatgctgg ggtcaagatt acaggaacaa atgctgaggt catgcctgcc      600
cagtgggaat ccaaatagg accctgtgaa ggaatccgca tggagatca tctctgggtg      660 gcccgtttca tcttgcatcg agtatgtgaa gactttgggg taatagcaac ctttgacccc      720
aagcccattc ctgggaactg gaatggtgca ggctgccata ccaactttag caccaaggcc      780
atgcgggagg agaatggtct gaagcacatc gaggaggcca tcgagaaact aagcaagcgg      840
caccggtacc acattcgagc ctacgatccc aagggggggcc tggacaatgc ccgtcgtctg      900
actgggttcc acgaaacgtc caacatcaac gactttttctg ctggtgtcgc caatcgcagt      960
gccagcatcc gcattccccg gactgtcggc caggagaaga aaggttactt tgaagaccgc     1020
```

-continued

```
cgcccctctg ccaattgtga cccctttgca gtgacagaag ccatcgtccg cacatgcctt      1080
ctcaatgaga ctggcgacga gcccttccaa tacaaaaact aa                        1122
```

```
<210> SEQ ID NO 4
<211> LENGTH: 204
<212> TYPE: DNA
<213> ORGANISM: Artificial Sequence
<220> FEATURE:
<223> OTHER INFORMATION: CMV promoter

<400> SEQUENCE: 4
gtgatgcggt tttggcagta catcaatggg cgtggatagc ggtttgactc acggggattt       60
ccaagtctcc accccattga cgtcaatggg agtttgtttt ggcaccaaaa tcaacgggac      120
tttccaaaat gtcgtaacaa ctccgcccca ttgacgcaaa tgggcggtag cgtgtacgg       180 tgggaggtct atataagcag agct                                             204
```

```
<210> SEQ ID NO 5
<211> LENGTH: 373
<212> TYPE: PRT
<213> ORGANISM: Artificial Sequence
<220> FEATURE:
<223> OTHER INFORMATION: CHO glutamine synthetase

<400> SEQUENCE: 5

Met Ala Thr Ser Ala Ser Ser His Leu Asn Lys Asn Ile Lys Gln Met
1               5                   10                  15

Tyr Leu Cys Leu Pro Gln Gly Glu Lys Val Gln Ala Met Tyr Ile Trp
            20                  25                  30

Val Asp Gly Thr Gly Glu Gly Leu Arg Cys Lys Thr Arg Thr Leu Asp
            35                  40                  45

Cys Glu Pro Lys Cys Val Glu Glu Leu Pro Glu Trp Asn Phe Asp Gly
        50                  55                  60

Ser Ser Thr Phe Gln Ser Glu Gly Ser Asn Ser Asp Met Tyr Leu Ser
65                  70                  75                  80

Pro Val Ala Met Phe Arg Asp Pro Phe Arg Arg Asp Pro Asn Lys Leu
                85                  90                  95

Val Phe Cys Glu Val Phe Lys Tyr Asn Arg Lys Pro Ala Glu Thr Asn
            100                 105                 110

Leu Arg His Ser Cys Lys Arg Ile Met Asp Met Val Ser Asn Gln His
        115                 120                 125

Pro Trp Phe Gly Met Glu Gln Glu Tyr Thr Leu Met Gly Thr Asp Gly
    130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Val Lys Ile Thr Gly
            180                 185                 190

Thr Asn Ala Glu Val Met Pro Ala Gln Trp Glu Phe Gln Ile Gly Pro
        195                 200                 205

Cys Glu Gly Ile Arg Met Gly Asp His Leu Trp Val Ala Arg Phe Ile
    210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255
```

```
Ser Thr Lys Ala Met Arg Glu Glu Asn Gly Leu Lys His Ile Glu Glu
        260                 265                 270

Ala Ile Glu Lys Leu Ser Lys Arg His Arg Tyr His Ile Arg Ala Tyr
        275                 280                 285

Asp Pro Lys Gly Gly Leu Asp Asn Ala Arg Gly Leu Thr Gly Phe His
        290                 295                 300

Glu Thr Ser Asn Ile Asn Asp Phe Ser Ala Gly Val Ala Asn Arg Ser
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Phe Ala Val Thr
        340                 345                 350

Glu Ala Ile Val Arg Thr Cys Leu Leu Asn Glu Thr Gly Asp Glu Pro
        355                 360                 365

Phe Gln Tyr Lys Asn
        370

<210> SEQ ID NO 6
<211> LENGTH: 286
<212> TYPE: PRT
<213> ORGANISM: Artificial Sequence
<220> FEATURE:
<223> OTHER INFORMATION: AmpR

<400> SEQUENCE: 6

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
        20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
        50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
        100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
        130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
        180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
        210                 215                 220

Ala Gly Trp Phe Ile Ala Asp Lys Ser Gly Ala Gly Glu Arg Gly Ser
225                 230                 235                 240
```

-continued

```
Arg Gly Ile Ile Ala Ala Leu Gly Pro Asp Gly Lys Pro Ser Arg Ile
            245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285

<210> SEQ ID NO 7
<211> LENGTH: 861
<212> TYPE: DNA
<213> ORGANISM: Artificial Sequence
<220> FEATURE:
<223> OTHER INFORMATION: AmpR

<400> SEQUENCE: 7
atgagtattc aacatttccg tgtcgccctt attccctttt ttgcggcatt ttgccttcct        60
gtttttgctc acccagaaac gctggtgaaa gtaaaagatg ctgaagatca gttgggtgca       120
cgagtgggtt acatcgaact ggatctcaac agcggtaaga tccttgagag ttttcgcccc       180
gaagaacgtt ttccaatgat gagcactttt aaagttctgc tatgtggcgc ggtattatcc       240
cgtattgacg ccgggcaaga gcaactcggt cgccgcatac actattctca gaatgacttg       300
gttgagtact caccagtcac agaaaagcat cttacggatg gcatgacagt aagagaatta       360
tgcagtgctg ccataaccat gagtgataac actgcggcca acttacttct gacaacgatc       420
ggaggaccga aggagctaac cgcttttttg cacaacatgg gggatcatgt aactcgcctt       480
gatcgttggg aaccggagct gaatgaagcc ataccaaacg acgagcgtga caccacgatg       540
cctgtagcaa tggcaacaac gttgcgcaaa ctattaactg gcgaactact tactctagct       600
tcccggcaac aattaataga ctggatggag gcggataaag ttgcaggacc acttctgcgc       660
tcggcccttc cggctggctg gtttattgct gataaatctg gagccggtga gcgtggttct       720
cgcggtatca ttgcagcact ggggccagat ggtaagccct cccgtatcgt agttatctac       780
acgacgggga gtcaggcaac tatggatgaa cgaaatagac agatcgctga gataggtgcc       840
tcactgatta gcattggta a                                                   861

<210> SEQ ID NO 8
<211> LENGTH: 861
<212> TYPE: DNA
<213> ORGANISM: Artificial Sequence
<220> FEATURE:
<223> OTHER INFORMATION: AmpR, complementary sequence

<400> SEQUENCE: 8
ttaccaatgc ttaatcagtg aggcacctat ctcagcgatc tgtctatttc gttcatccat        60
agttgcctga ctccccgtcg tgtagataac tacgatacgg gagggcttac catctggccc       120
cagtgctgca atgataccgc gagaaccacg ctcaccggct ccagatttat cagcaataaa       180
ccagccagcc ggaagggccg agcgcagaag tggtcctgca actttatccg cctccatcca       240
gtctattaat tgttgccggg aagctagagt aagtagttcg ccagttaata gtttgcgcaa       300
cgttgttgcc attgctacag catcgtggt gtcacgctcg tcgtttggta tggcttcatt        360
cagctccggt tcccaacgat caaggcgagt tacatgatcc cccatgttgt gcaaaaaagc       420
ggttagctcc ttcggtcctc cgatcgttgt cagaagtaag ttggccgcag tgttatcact       480
catggttatg gcagcactgc ataattctct tactgtcatg ccatccgtaa gatgcttttc       540
tgtgactggt gagtactcaa ccaagtcatt ctgagaatag tgtatgcggc gaccgagttg       600
```

-continued

```
ctcttgcccg gcgtcaatac gggataatac cgcgccacat agcagaactt taaaagtgct      660
catcattgga aaacgttctt cggggcgaaa actctcaagg atcttaccgc tgttgagatc      720
cagttcgatg taacccactc gtgcacccaa ctgatcttca gcatctttta ctttcaccag      780
cgtttctggg tgagcaaaaa caggaaggca aaatgccgca aaaaagggaa taagggcgac      840
acggaaatgt tgaatactca t                                               861
```

```
<210> SEQ ID NO 9
<211> LENGTH: 105
<212> TYPE: DNA
<213> ORGANISM: Artificial Sequence
<220> FEATURE:
<223> OTHER INFORMATION: AmpR promoter

<400> SEQUENCE: 9
cgcggaaccc ctatttgttt attttttctaa atacattcaa atatgtatcc gctcatgaga       60
caataaccct gataaatgct tcaataatat tgaaaaagga agagt                       105
```

```
<210> SEQ ID NO 10
<211> LENGTH: 105
<212> TYPE: DNA
<213> ORGANISM: Artificial Sequence
<220> FEATURE:
<223> OTHER INFORMATION: AmpR promoter complementary sequence

<400> SEQUENCE: 10
actcttcctt tttcaatatt attgaagcat ttatcagggt tattgtctca tgagcggata       60
catatttgaa tgtatttaga aaaataaaca aatagggggtt ccgcg                      105
```

```
<210> SEQ ID NO 11
<211> LENGTH: 589
<212> TYPE: DNA
<213> ORGANISM: Artificial Sequence
<220> FEATURE:
<223> OTHER INFORMATION: ori

<400> SEQUENCE: 11
ttgagatcct ttttttctgc gcgtaatctg ctgcttgcaa acaaaaaaac caccgctacc       60
agcggtggtt tgtttgccgg atcaagagct accaactctt tttccgaagg taactggctt      120
cagcagagcg cagataccaa atactgtcct tctagtgtag ccgtagttag gccaccactt      180
caagaactct gtagcaccgc ctacatacct cgctctgcta atcctgttac cagtggctgc      240
tgccagtggc gataagtcgt gtcttaccgg gttggactca agacgatagt taccggataa      300
ggcgcagcgg tcgggctgaa cggggggttc gtgcacacag cccagcttgg agcgaacgac      360
ctacaccgaa ctgagatacc tacagcgtga gctatgagaa agcgccacgc ttcccgaagg      420
gagaaaggcg gacaggtatc cggtaagcgg cagggtcgga acaggagagc gcacgaggga      480
gcttccaggg ggaaacgcct ggtatcttta tagtcctgtc gggtttcgcc acctctgact      540
tgagcgtcga tttttgtgat gctcgtcagg gggcggagc ctatggaaa                   589
```

```
<210> SEQ ID NO 12
<211> LENGTH: 589
<212> TYPE: DNA
<213> ORGANISM: Artificial Sequence
<220> FEATURE:
<223> OTHER INFORMATION: ori complementary sequence
```

-continued

<400> SEQUENCE: 12

```
tttccatagg ctccgccccc ctgacgagca tcacaaaaat cgacgctcaa gtcagaggtg      60
gcgaaacccg acaggactat aaagatacca ggcgtttccc cctggaagct ccctcgtgcg     120
ctctcctgtt ccgaccctgc cgcttaccgg atacctgtcc gcctttctcc cttcgggaag     180
cgtggcgctt tctcatagct cacgctgtag gtatctcagt tcggtgtagg tcgttcgctc     240
caagctgggc tgtgtgcacg aaccccccgt tcagcccgac cgctgcgcct tatccggtaa     300
ctatcgtctt gagtccaacc cggtaagaca cgacttatcg ccactggcag cagccactgg     360
taacaggatt agcagagcga ggtatgtagg cggtgctaca gagttcttga agtggtggcc     420
taactacggc tacactagaa ggacagtatt tggtatctgc gctctgctga agccagttac     480
cttcggaaaa agagttggta gctcttgatc cggcaaacaa accaccgctg gtagcggtgg     540 ttttttttgtt tgcaagcagc agattacgcg cagaaaaaaa ggatctcaa              589
```

<210> SEQ ID NO 13
<211> LENGTH: 3603
<212> TYPE: DNA
<213> ORGANISM: Artificial Sequence
<220> FEATURE:
<223> OTHER INFORMATION: EASE

<400> SEQUENCE: 13

```
caattctaca gaaaattgtt gcacctgttc agagtctaat tattgttttg caggcacagt      60
atgacaagta agtatctgtt gaatacattg taattcctaa attctatgga acttaaattt     120
gttctcagga tacaaaatgt acttgaaatt ttccttattt accttgtaaa cataataaaa     180
gttggtatta aaccataaag tttataacac caagcaaata attcaaacta acatggctca     240
tacatgaagt catctggcta aagaatgttt cttgaagttt atttctagaa cagcaaatgc     300
caactatctt ttaaaaaaat aatttaagaa aatgagcaaa agagcagttt aattaagtaa     360
cacctaatta gctttaagga gaccaaggca aagcctgcca aaagattaac accattactt     420
atctgttcga aaactactga cgacttacat tctggatgta tttaaaaaaa aaaaaaaaaa     480
ctaaattgct ttatcctatc aagttgtaca agatacccac gagacagaca atatagtatg     540
tcaatcagtt aagacgttaa atgacaaaaa catgttaaat caaaaataat tcttctttcc     600
tgctattttt aaatgttata aaatgcagct aggagctttt actattactc tgtggtgcaa     660
agtctacatg gtaattggca gcagccaaaa cagaatggca taccggcact tgatattgct     720
gtgtaaagaa aatataagtt tccagaggta caaaaatact actttgcagg tgccaaccaa     780
ccaccaggac tttagctggc tgtaaaggca gcttatttct gcaatcaaac cgaaagcatt     840
ttcacacaga agatggagtc tgcagcccta tgtgatctga agcagggcta atctgcacag     900
agcaaacaat cagggagggc cagccctgct gggaaggtcg cattctccca cagcaacaag     960
gcagggcaac taagcagcac attgcagcaa gaggacaaca gacagcctgt ccccagaacc    1020
gcccagccgc atgcacaaca accaacagag gattcagagc aaggggatgc tcttacctct    1080
tttatgtaat tccctcaagg ggatattgtc tcctcccccg tcataaggca aatagggatc    1140
ggaagaagca tccatgatca gaattttttt aaaagaaaaa aaaaaagatg aagaaaagag    1200
aagcttgcta gattaaaaag atggtggcat ttttttcctcc ccctgctata gcaggcaagg    1260
gagatgccat atttgatgag gttggaactg tatagttcga ctggctgaag caactgggtt    1320
cttccacagt ggatgatgtc atcaaaggga aattattgca gcctggttgc tagtggctac    1380
```

```
aatctagccc ggcttagagg cagcacagcc ttcttaatca ggtcctgttg tgtacgacga    1440
tgactaagcg ccaagtataa caggcgaaac tgctttgaga aatttaaagt gctcacaacg    1500
tagtttcagt agtaagacag cagaaacatt tattttttatt tggaaaaaat ataagacata    1560
aaaaggtaat tccaaatgct aacaatggca ctttagccaa acagaaaact ctaaaaaggc    1620
tatgttttta taaatgtact aatttatgca taaattcatg agtcataaca gtgaaaacta    1680
aagcacacca acaagtttct ccagagtctt ggctttaaga atttgtttaa ttttcctttta    1740 atccttttat ggaaaattta aatgctgagt cactgagttg aatgagtggt gttttatctc    1800
atttaccaat cccctccagc ggcctcccgt tcccttttttc aaacccagcc acaagacact    1860
ccagttgggg gaaaaagtga aaacttaccc gtatactaat aactcctaca tgtgcaaatt    1920
atgcaaaaag attaactacg taggagacg tctattttgc tgtttttccaa cttacagaag    1980 attatgtact tagaaagact tttagtagaa aaatgtctat caaagttagc tactcccact    2040
gtctctgtgc tagaaaattt taagtttaga aatgtaactt ttgtttttaat acggcattcc    2100 aaacataact agtgctcatg agtgatagga gttcagggtt tacagattcc tctaaggcgg    2160
ggtctctgac tggagcagtc ttctaaaatg cctgttatgt agtgcaatta gtaaataaag    2220
ggtgatgtcc accacgaact tgggcacagg gtctataaaa tgtgttttct tcaggcatga    2280
atgaatcaac ctctaagatc cgctccaact ctgcatatct gaaaactgca ggtaagaaga    2340
gaggaataaa gtctattcat ttagcctggt ctgtttttcag ttgttctgga gtcttttctc    2400
tcccaagttt gttaagttag ataggtttct atatttcaaa agcttgaaac tcaaacaaaa    2460
gtccacaggg aatctggaag tcaagactcc aggaaaagaa tccagaccag aactaggatg    2520
acagggaatt acattttaag caaggaaagc tttgacaaag ccaatttttac tgaactagtt    2580 cagtgtgaat ttggtcattt gctgttctct ggtataatat atactgcata gcactcattt    2640
cacctgcatg agactatttt cttactcgcc ttaccagaac atgagaaacc ttcccacaaa    2700
cctccctggc atttgtgcac tctctccaaa cttggtcaca aagaatgaag aggacagtac    2760
tagaggagga atattacgcc tgtgaaatgt tgacaatgcc aagtgaactt tgtagctata    2820
ctgacttact tttcaagata aaaaaaaaat catgtgcata tgatatatat tattgtgcta    2880
gcatttgcac agaggtagtt ttagaataag acaaagttta acagctgtta tcactgagca    2940
atgaggcaga agaggaaagt gggcttgcac tcactactaa tcagctagag atcaggttaa    3000
ctgagaggag attccaagat tggacccagg gcctcctgca tgctgagtgt gtgctctacc    3060
cctgggttgc atctccagct cttcattaga atttttttaaa cgaacatatt acttttataa    3120
taatgaaagt gaatttctttt ctatttcctg ttattcatgc ataacaggat tcacagaaga    3180
cacttcctct tcggacacat ttggaaacac aaggcagtaa gccttacttt acagttagcc    3240
ctcttgccta agagaaagcc gagggggaag aaagagagca aagctttcag aaaaggaatc    3300
cattaaagct acagagatgc ttcgaagtta gaacaccatg aaacaaagaa gcactaagag    3360
gtctaagacg taaaccctcc ccaaaaagcc aagcctacaa taaactgaaa ttacaaagta    3420
attctgtgat gttcgtacct cataaagttt tagatcctca cctacgcaaa catactttgc    3480
agtcgctctt tagaaaaggg caaggtacaa tggaaggaga gacaggactg tgaccaggaa    3540
attaaaatgg attacaatta gggtgtggta gaagggaagg gaacaaaaga aaagttcaga    3600
att                                                                  3603
```

<210> SEQ ID NO 14
<211> LENGTH: 3603

-continued

```
<212> TYPE: DNA
<213> ORGANISM: Artificial Sequence
<220> FEATURE:
<223> OTHER INFORMATION: EASE complementary sequence

<400> SEQUENCE: 14
aattctgaac ttttcttttg ttcccttccc ttctaccaca ccctaattgt aatccatttt        60
aatttcctgg tcacagtcct gtctctcctt ccattgtacc ttgccctttt ctaaagagcg       120
actgcaaagt atgtttgcgt aggtgaggat ctaaaacttt atgaggtacg aacatcacag       180
aattactttg taatttcagt ttattgtagg cttggctttt tggggagggt ttacgtctta       240
gacctcttag tgcttctttg tttcatggtg ttctaacttc gaagcatctc tgtagcttta       300
atggattcct tttctgaaag ctttgctctc tttcttcccc ctcggctttc tcttaggcaa       360
gagggctaac tgtaaagtaa ggcttactgc cttgtgtttc caaatgtgtc cgaagaggaa       420
gtgtcttctg tgaatcctgt tatgcatgaa taacaggaaa tagaaagaaa ttcactttca       480
ttattataaa agtaatatgt tcgtttaaaa aattctaatg aagagctgga gatgcaaccc       540
aggggtagag cacacactca gcatgcagga ggccctgggt ccaatcttgg aatctcctct       600
cagttaacct gatctctagc tgattagtag tgagtgcaag cccactttcc tcttctgcct       660
cattgctcag tgataacagc tgttaaactt tgtcttattc taaaactacc tctgtgcaaa       720
tgctagcaca ataatatata tcatatgcac atgatttttt ttttatcttg aaaagtaagt       780
cagtatagct acaaagttca cttggcattg tcaacatttc acaggcgtaa tattcctcct       840
ctagtactgt cctcttcatt ctttgtgacc aagtttggag agagtgcaca aatgccaggg       900
aggtttgtgg gaaggtttct catgttctgg taaggcgagt aagaaaatag tctcatgcag       960
gtgaaatgag tgctatgcag tatatattat accagagaac agcaaatgac caaattcaca      1020
ctgaactagt tcagtaaaat tggctttgtc aaagctttcc ttgcttaaaa tgtaattccc      1080
tgtcatccta gttctggtct ggattctttt cctggagtct tgacttccag attccctgtg      1140
gacttttgtt tgagtttcaa gcttttgaaa tatagaaacc tatctaactt aacaaacttg      1200
ggagagaaaa gactccagaa caactgaaaa cagaccaggc taaatgaata gactttattc      1260
ctctcttctt acctgcagtt ttcagatatg cagagttgga gcggatctta gaggttgatt      1320
cattcatgcc tgaagaaaac acattttata gaccctgtgc ccaagttcgt ggtggacatc      1380 acccttttatt tactaattgc actacataac aggcatttta gaagactgct ccagtcagag      1440
accccgcctt agaggaatct gtaaaccctg aactcctatc actcatgagc actagttatg      1500
tttggaatgc cgtattaaaa caaaagttac atttctaaac ttaaaatttt ctagcacaga      1560
gacagtggga gtagctaact ttgatagaca ttttttctact aaaagtcttt ctaagtacat      1620
aatcttctgt aagttggaaa acagcaaaat agaacgtctc ctacgtagtt aatctttttg      1680
cataatttgc acatgtagga gttattagta tacgggtaag ttttcacttt ttcccccaac      1740
tggagtgtct tgtggctggg tttgaaaaag ggaacgggag gccgctggag gggattggta      1800
aatgagataa aacaccactc attcaactca gtgactcagc atttaaattt tccataaaag      1860
gattaaagga aaattaaaca aattcttaaa gccaagactc tggagaaact tgttggtgtg      1920
ctttagtttt cactgttatg actcatgaat ttatgcataa attagtacat ttataaaaac      1980
atagcctttt tagagttttc tgtttggcta aagtgccatt gttagcattt ggaattacct      2040
ttttatgtct tatattttttt ccaaataaaa ataaatgttt ctgctgtctt actactgaaa      2100
ctacgttgtg agcactttaa atttctcaaa gcagtttcgc ctgttatact tggcgcttag      2160
```

-continued

```
tcatcgtcgt acacaacagg acctgattaa gaaggctgtg ctgcctctaa gccgggctag    2220
attgtagcca ctagcaacca ggctgcaata atttcccttt gatgacatca tccactgtgg    2280
aagaacccag ttgcttcagc cagtcgaact atacagttcc aacctcatca aatatggcat    2340
ctcccttgcc tgctatagca gggggaggaa aaaatgccac catctttta atctagcaag     2400 cttctctttt cttcatcttt ttttttttct tttaaaaaaa ttctgatcat ggatgcttct    2460
tccgatccct atttgcctta tgacggggga ggagacaata tccccttgag ggaattacat    2520
aaaagaggta agagcatccc cttgctctga atcctctgtt ggttgttgtg catgcggctg    2580
ggcggttctg gggacaggct gtctgttgtc ctcttgctgc aatgtgctgc ttagttgccc     2640
tgccttgttg ctgtgggaga atgcgacctt cccagcaggg ctggccctcc ctgattgttt    2700
gctctgtgca gattagccct gcttcagatc acatagggct gcagactcca tcttctgtgt    2760
gaaaatgctt tcggtttgat tgcagaaata agctgccttt acagccagct aaagtcctgg    2820
tggttggttg gcacctgcaa agtagtattt ttgtacctct ggaaacttat attttctta    2880 cacagcaata tcaagtgccg gtatgccatt ctgttttggc tgctgccaat taccatgtag    2940
actttgcacc acagagtaat agtaaaagct cctagctgca ttttataaca tttaaaaata    3000
gcaggaaaga agaattattt ttgatttaac atgttttgt catttaacgt cttaactgat     3060
tgacatacta tattgtctgt ctcgtgggta tcttgtacaa cttgatagga taaagcaatt    3120
tagttttttt tttttttttt aaatacatcc agaatgtaag tcgtcagtag ttttcgaaca    3180
gataagtaat ggtgttaatc ttttggcagg ctttgccttg gtctccttaa agctaattag    3240
gtgttactta attaaactgc tctttgctc attttcttaa attattttt taaaagatag      3300 ttggcatttg ctgttctaga aataaacttc aagaaacatt ctttagccag atgacttcat    3360
gtatgagcca tgttagtttg aattatttgc ttggtgttat aaactttatg gtttaatacc    3420 aactttatt atgtttacaa ggtaaataag gaaaatttca agtacatttt gtatcctgag     3480
aacaaattta agttccatag aatttaggaa ttacaatgta ttcaacagat acttacttgt    3540
catactgtgc ctgcaaaaca ataattagac tctgaacagg tgcaacaatt ttctgtagaa    3600
ttg                                                                  3603
```

<210> SEQ ID NO 15
<211> LENGTH: 3608
<212> TYPE: DNA
<213> ORGANISM: Artificial Sequence
<220> FEATURE:
<223> OTHER INFORMATION: EASE

<400> SEQUENCE: 15

```
gatctaattc tgaacttttc ttttgttccc ttcccttcta ccacaccta attgtaatcc      60 attttaattt cctggtcaca gtcctgtctc tccttccatt gtaccttgcc cttttctaaa    120
gagcgactgc aaagtatgtt tgcgtaggtg aggatctaaa actttatgag gtacgaacat    180
cacagaatta ctttgtaatt tcagtttatt gtaggcttgg cttttgggg agggtttacg      240 tcttagacct cttagtgctt ctttgtttca tggtgttcta acttcgaagc atctctgtag    300
ctttaatgga ttccttttct gaaagctttg ctctcttct tccccctcgg ctttctctta     360
ggcaagaggg ctaactgtaa agtaaggctt actgccttgt gtttccaaat gtgtccgaag    420
aggaagtgtc ttctgtgaat cctgttatgc atgaataaca ggaaatagaa agaaattcac    480
tttcattatt ataaaagtaa tatgttcgtt taaaaaattc taatgaagag ctggagatgc    540
aacccagggg tagagcacac actcagcatg caggaggccc tgggtccaat cttggaatct    600
```

```
cctctcagtt aacctgatct ctagctgatt agtagtgagt gcaagcccac tttcctcttc      660
tgcctcattg ctcagtgata acagctgtta aactttgtct tattctaaaa ctacctctgt      720
gcaaatgcta gcacaataat atatatcata tgcacatgat ttttttttta tcttgaaaag      780
taagtcagta tagctacaaa gttcacttgg cattgtcaac atttcacagg cgtaatattc      840
ctcctctagt actgtcctct tcattctttg tgaccaagtt tggagagagt gcacaaatgc      900
cagggaggtt tgtgggaagg tttctcatgt tctggtaagg cgagtaagaa aatagtctca      960
tgcaggtgaa atgagtgcta tgcagtatat attataccag agaacagcaa atgaccaaat     1020
tcacactgaa ctagttcagt aaaattggct ttgtcaaagc tttccttgct aaaatgtaa      1080 ttccctgtca tcctagttct ggtctggatt cttttcctgg agtcttgact tccagattcc     1140
ctgtggactt ttgtttgagt ttcaagcttt tgaaatatag aaacctatct aacttaacaa     1200
acttgggaga gaaaagactc cagaacaact gaaaacagac caggctaaat gaatagactt     1260
tattcctctc ttcttacctg cagttttcag atatgcagag ttggagcgga tcttagaggt     1320
tgattcattc atgcctgaag aaaacacatt ttatagaccc tgtgcccaag ttcgtggtgg     1380
acatcaccct ttatttacta attgcactac ataacaggca ttttagaaga ctgctccagt     1440
cagagacccc gccttagagg aatctgtaaa ccctgaactc ctatcactca tgagcactag     1500
ttatgtttgg aatgccgtat taaaacaaaa gttacatttc taaacttaaa attttctagc     1560
acagagacag tgggagtagc taactttgat agacattttt ctactaaaag tctttctaag     1620
tacataatct tctgtaagtt ggaaaacagc aaaatagaac gtctcctacg tagttaatct     1680
ttttgcataa tttgcacatg taggagttat tagtatacgg gtaagttttc actttttccc     1740
ccaactggag tgtcttgtgg ctgggtttga aaaagggaac gggaggccgc tggaggggat     1800
tggtaaatga gataaaacac cactcattca actcagtgac tcagcattta aattttccat     1860
aaaaggatta aaggaaaatt aaacaaattc ttaaagccaa gactctggag aaacttgttg     1920 gtgtgctttta gttttcactg ttatgactca tgaatttatg cataaattag tacatttata     1980
aaaacatagc ctttttagag ttttctgttt ggctaaagtg ccattgttag catttggaat     2040 tacctttttta tgtcttatat tttttccaaa taaaaataaa tgtttctgct gtcttactac     2100
tgaaactacg ttgtgagcac tttaaatttc tcaaagcagt ttcgcctgtt atacttggcg     2160
cttagtcatc gtcgtacaca acaggacctg attaagaagg ctgtgctgcc tctaagccgg     2220
gctagattgt agccactagc aaccaggctg caataatttc cctttgatga catcatccac     2280
tgtggaagaa cccagttgct tcagccagtc gaactataca gttccaacct catcaaatat     2340
ggcatctccc ttgcctgcta tagcaggggg aggaaaaaat gccaccatct ttttaatcta     2400
gcaagcttct ctttttcttca tcttttttttt tttcttttaa aaaaattctg atcatggatg     2460
cttcttccga tccctatttg ccttatgacg ggggaggaga caatatcccc ttgagggaat     2520
tacataaaag aggtaagagc atccccttgc tctgaatcct ctgttggttg ttgtgcatgc     2580
ggctgggcgg ttctggggac aggctgtctg ttgtcctctt gctgcaatgt gctgcttagt     2640
tgccctgcct tgttgctgtg ggagaatgcg accttcccag cagggctggc cctccctgat     2700
tgtttgctct gtgcagatta gccctgcttc agatcacata gggctgcaga ctccatcttc     2760
tgtgtgaaaa tgctttcggt ttgattgcag aaataagctg cctttacagc cagctaaagt     2820
cctggtggtt ggtggcacc tgcaaagtag tattttttgta cctctggaaa cttatatttt      2880
ctttacacag caatatcaag tgccggtatg ccattctgtt ttggctgctg ccaattacca     2940
```

-continued

```
tgtagacttt gcaccacaga gtaatagtaa aagctcctag ctgcatttta taacatttaa    3000
aaatagcagg aaagaagaat tatttttgat ttaacatgtt tttgtcattt aacgtcttaa    3060
ctgattgaca tactatattg tctgtctcgt gggtatcttg tacaacttga taggataaag    3120
caatttagtt ttttttttttt ttttttaaata catccagaat gtaagtcgtc agtagttttc   3180
gaacagataa gtaatggtgt taatcttttg gcaggctttg ccttggtctc cttaaagcta    3240
attaggtgtt acttaattaa actgctcttt tgctcatttt cttaaattat tttttttaaaa  3300 gatagttggc atttgctgtt ctagaaataa acttcaagaa acattcttta gccagatgac    3360
ttcatgtatg agccatgtta gtttgaatta tttgcttggt gttataaact ttatggttta    3420
ataccaactt ttattatgtt tacaaggtaa ataaggaaaa tttcaagtac attttgtatc     3480
ctgagaacaa atttaagttc catagaattt aggaattaca atgtattcaa cagatactta    3540
cttgtcatac tgtgcctgca aaacaataat tagactctga acaggtgcaa caattttctg    3600
tagaattg                                                            3608
```

```
<210> SEQ ID NO 16
<211> LENGTH: 19
<212> TYPE: DNA
<213> ORGANISM: Artificial Sequence
<220> FEATURE:
<223> OTHER INFORMATION: T7 promoter

<400> SEQUENCE: 16
taatacgact cactatagg                                                      19
```